(12) United States Patent
Miki et al.

(10) Patent No.: US 10,716,885 B2
(45) Date of Patent: Jul. 21, 2020

(54) HEMOFILTRATION DEVICE

(71) Applicants: KEIO UNIVERSITY, Tokyo (JP); TOKYO MEDICAL UNIVERSITY, Tokyo (JP)

(72) Inventors: Norihisa Miki, Yokohama (JP); Yoshihiko Kanno, Tokyo (JP)

(73) Assignees: KEIO UNIVERSITY, Tokyo (JP); TOKYO MEDICAL UNIVERSITY, Tokyo (JP)

( * ) Notice: Subject to any disclaimer, the term of this patent is extended or adjusted under 35 U.S.C. 154(b) by 340 days.

(21) Appl. No.: 15/445,222

(22) Filed: Feb. 28, 2017

(65) Prior Publication Data
US 2017/0258977 A1 Sep. 14, 2017

(30) Foreign Application Priority Data
Mar. 9, 2016 (JP) .................................. 2016-046355

(51) Int. Cl.
*A61M 1/16* (2006.01)
*B01D 67/00* (2006.01)
(Continued)

(52) U.S. Cl.
CPC ........ *A61M 1/1678* (2013.01); *A61M 1/1631* (2014.02); *A61M 1/34* (2013.01);
(Continued)

(58) Field of Classification Search
CPC .... A61M 1/1678; A61M 1/1631; A61M 1/34; B01D 63/082; B01D 63/087;
(Continued)

(56) References Cited

U.S. PATENT DOCUMENTS 5,092,886 A * 3/1992 Dobos-Hardy ......... A61F 2/022
623/23.65
2007/0092399 A1* 4/2007 Yokomine .............. G01N 21/05
422/400
(Continued)

FOREIGN PATENT DOCUMENTS

JP H03-505532 A 12/1991
JP 2011-104346 A 6/2011
(Continued)

OTHER PUBLICATIONS

Ota et al., "Biofouling of micro channel in implantable artificial kidney," the Japan Society of Mechanical Engineers, 7th symposium on micro-nano science and technology, Oct. 28-30, 2015, Nigata, Japan (English translation included) (6 pages).

*Primary Examiner* — Ariana Zimbouski
(74) *Attorney, Agent, or Firm* — Lucas & Mercanti, LLP

(57) ABSTRACT

A hemofiltration device capable of surely performing highly-efficient hemofiltration. The hemofiltration device of the present invention is adapted to be implanted in a mammalian body for filtering blood, and includes a blood flow path layer having a blood flow path, a filtrate flow path layer having a filtrate flow path disposed along the blood flow path, and a filtration membrane interposed between the blood flow path layer and the filtrate flow path layer, for filtering the blood flowing through the blood flow path. A filtrate outlet of the filtrate flow path is provided at a position closer to a blood outlet than to a blood inlet of the blood flow path. The blood inlet, blood outlet, and filtrate outlet are provided only on one side or separately on opposite sides of a main body portion in the direction in which the layers are stacked.

24 Claims, 22 Drawing Sheets

(51) Int. Cl.
    *A61M 1/34*     (2006.01)
    *B01D 63/08*     (2006.01)
    *B01D 69/06*     (2006.01)
    *B01D 71/52*     (2006.01)
    *B01D 71/68*     (2006.01)

(52) U.S. Cl.
    CPC ......... *B01D 63/082* (2013.01); *B01D 63/087* (2013.01); *B01D 67/0088* (2013.01); *B01D 69/06* (2013.01); *B01D 71/52* (2013.01); *B01D 71/68* (2013.01); *A61M 2205/0244* (2013.01); *A61M 2205/04* (2013.01); *A61M 2205/75* (2013.01); *B01D 2313/086* (2013.01); *B01D 2325/02* (2013.01)

(58) Field of Classification Search
    CPC .... B01D 67/0088; B01D 69/06; B01D 71/52; B01D 71/68
    See application file for complete search history.

(56) References Cited

U.S. PATENT DOCUMENTS

2011/0011786 A1*   1/2011   Feichtner ........... A61B 5/14528
                                                    210/321.84
2014/0358060 A1*  12/2014  Laster .................... A61M 1/34
                                                       604/6.09

FOREIGN PATENT DOCUMENTS

| WO | 2000/043052 A1 | 7/2000 |
| WO | 2013/098823 A2 | 7/2013 |

* cited by examiner

Direction in which layers are stacked

Direction in which layers are stacked

HEMOFILTRATION DEVICE

CROSS-REFERENCE TO RELATED APPLICATION

The present application claims priority from Japanese patent application JP2016-046355 filed on Mar. 9, 2016, the content of which is hereby incorporated by reference into this application.

BACKGROUND

Technical Field

The present invention relates to a hemofiltration device for filtering blood of humans or animals.

Background Art

Most of patients with chronic kidney disease undergo dialysis treatment. It has been said that 0.3 million patients with kidney disease currently need dialysis treatment and that 10 million people are future potential patients with kidney disease. The dialysis treatment is a well-established treatment in which blood is taken out from a body and purified by a dialysis system, and then returned to the body. It has even been said that patients on the dialysis treatment would not die from kidney disease.

However, there is a problem that the patients have to go to the hospital three days a week and need a four-hour rest in bed each time of the dialysis treatment. This restricts their life to cause the QoL to be substantially reduced. Further, as compared to healthy people, whose blood is purified for 24 hours for seven days, the patients have their blood rapidly and intensively purified for 12 hours a week. This puts an enormous load on their blood vessels or the like.

Patent Document 1 discloses a technique of storing dialysate, an absorbent, an enzyme, and the like in a bag formed of a dialysis membrane and placing the bag inside a human or animal body.

RELATED ART DOCUMENTS

Patent Documents

Patent Document 1: JP 2011-104346 A

SUMMARY

The inventors have conducted concentrated studies and accomplished an invention of a hemofiltration device capable of surely performing highly-efficient hemofiltration.

In order to solve the forgoing problem, the hemofiltration device of the present invention is adapted to be implanted in a mammalian body for filtering blood, and includes: a blood flow path layer having a blood flow path; a filtrate flow path layer having a filtrate flow path that is disposed along the blood flow path; and a filtration membrane interposed between the blood flow path layer and the filtrate flow path layer, the filtration membrane being adapted to filter the blood flowing through the blood flow path. A filtrate outlet of the filtrate flow path is provided at a position closer to a blood outlet than to a blood inlet of the blood flow path. According to the present invention, the blood can be prevented from being mixing into the filtrate to be discharged from the filtrate outlet.

Further, the hemofiltration device of the present invention includes a main body portion in which the blood flow path layer having the blood flow path and the filtrate flow path layer having the filtrate flow path are alternately stacked with the filtration membrane interposed therebetween. The blood inlet, the blood outlet, and the filtrate outlet are provided only on one side or separately on opposite sides of the main body portion in the direction in which the layers are stacked. According to the present invention, the position of the filtrate outlet can be selected in accordance with the position and posture of the device to be mounted, and the lengths of tubes to be connected to the blood flow path and the filtrate flow path can be reduced.

The hemofiltration device of the present invention is preferably configured such that the main body portion has a pentagonal or more polygonal outline or a circular outline and is integrally formed in a state compressed in the stacked direction of the layers, by means of five or more fastening means equidistantly disposed along the outline. According to the present invention, the main body portion can be uniformly compressed across its entire periphery in the stacked direction of the layers, so that leakage of the blood can be prevented.

In the hemofiltration device of the present invention, the blood flow path has at least one fold-back portion, where the radius of curvature of the wall surface on the outer periphery side of the flow path is preferably larger than that on the inner periphery side of the flow path. According to the present invention, the blood flow is smooth in the fold-back portion, and biofouling can thus be suppressed.

In the hemofiltration device of the present invention, the blood flow path layer and the filtrate flow path layer each have a slot and the slots of the layers at least partially overlap each other. Each of the slots of the blood flow path layer and filtrate flow path layer preferably has one of a zigzag shape, a tree shape, or a concentric circular shape. According to the present invention, long lengths of the flow paths can be secured so that an improved filtration rate can be obtained.

In the hemofiltration device of the present invention, the surface roughness of the wall surface of the blood flow path preferably has one of a maximum height Rz of 0.01 to 10 μm, inclusive or an arithmetic average roughness Ra of 0.01 to 3 μm, inclusive. According to the present invention, a decrease in the filtration efficiency caused by an excessively accelerated blood flow rate as well as adhesion of blood or blood components to the wall surface can be prevented.

According to the present invention, highly-efficient hemofiltration can be surely performed. Further features of the present invention will become apparent from the description of the present specification and attached drawings. Further, problems, configurations, and advantageous effects other than those described above will become apparent from the following description of embodiments.

DETAILED DESCRIPTION

Next, an embodiment of the present invention will be described with reference to the drawings.

Figure 1:
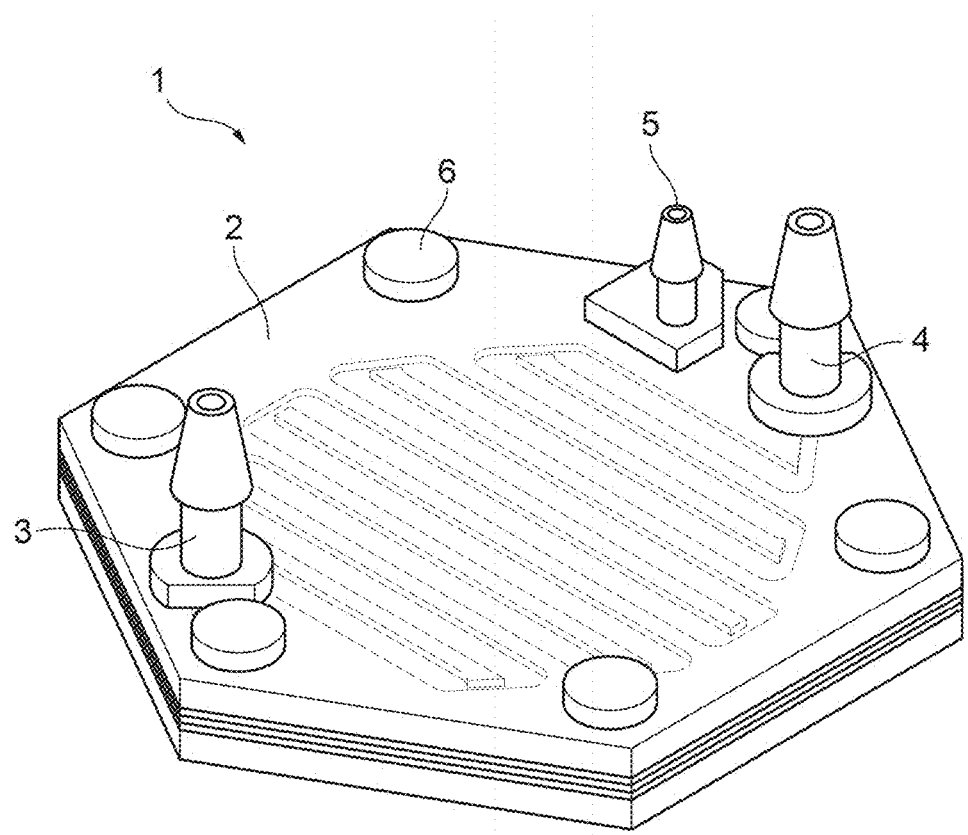
FIG. 1 is an overall perspective view illustrating an embodiment of a hemofiltration device according to the present invention.
Figure 2:
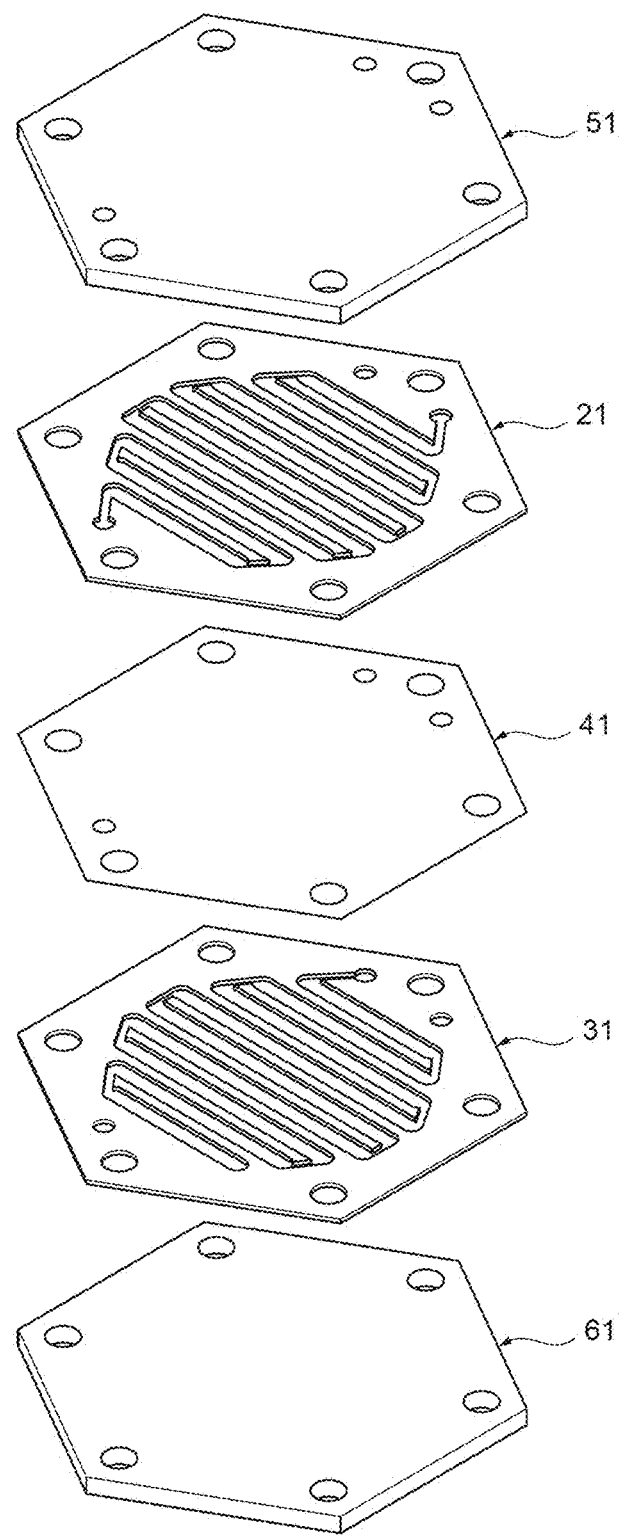
FIG. 2 is an exploded perspective view of a main body portion.

FIG. 1 is an overall perspective view illustrating an embodiment of the hemofiltration device according to the present invention. FIG. 2 is an exploded perspective view of the main body portion.

<Overall Configuration>

A hemofiltration device 1 is an implantable device, which is adapted to be embedded, for use, in the bodies of mammals, such as humans, dogs, or cats, whose kidney function has been degraded, for example. The hemofiltration device 1 has a structure in which blood is filtered and filtrate taken out from the blood is discharged to the outside of the body directly or through the bladder.

As shown in FIG. 1, the hemofiltration device 1 includes a main body portion 2 having a regular hexagonal outline. The main body portion 2 has a stacked structure of a plurality of plate-like members. Further, on a surface on one side of the main body portion 2 in the direction in which the stacked structure is formed, a blood inlet 3, a blood outlet 4, and a filtrate outlet 5 are provided. The blood inlet 3 allows the blood to flow into the main body portion 2 and the blood outlet 4 allows the blood inside the main body portion 2 to flow out, and the filtrate outlet 5 discharges filtrate that has been taken out from the blood through the hemofiltration inside the main body portion 2. Each of the blood inlet 3, blood outlet 4, and filtrate outlet 5 has a shape of a connector so that a tube can be connected thereto.

<Configuration of the Main Body Portion>

As shown in FIG. 2, the main body portion 2 has a stacked structure in which a blood flow path layer 21 and a filtrate flow path layer 31 are alternately stacked with a filtration membrane 41 interposed therebetween. It should be noted that although FIG. 2 shows, for simple explanation of the structure, an example of a configuration in which one blood flow path layer 21 and one filtrate flow path layer 31 are prepared and stacked, the structure is not limited to this configuration. The main body portion 2 may have a configuration in which a plurality of blood flow path layers 21 and a plurality of filtrate flow path layers 31 are prepared and alternately stacked so that the resulting stacked structure has several tens or hundreds of layers. The number of the stacked layers can be changed, as appropriate, depending on the mammal on which the hemofiltration device 1 is mounted.

Specifically, when it is considered that the amount of the blood flow of a mammal as a subject is relatively small (for example, when the body weighs 0.5 kg or greater and 20 kg or less), the number of the stacked layers may be, for example, 1 to 120, 2 to 60, 5 to 30, or 5 to 20, inclusive. Meanwhile, when the subject is a human (an adult, in particular) weighing 20 kg or greater and 100 kg or less, for example, the number of the stacked layers may be, for example, 1 to 300, 1 to 240, 1 to 120, or 2 to 60, inclusive.

The main body portion 2 is sandwiched between a first end plate 51 and a second end plate 61 from opposite sides of the stacked direction of the layers, and is integrally formed by means of fastening means, such as bolts 6 and nuts (not shown), and retained in a state compressed in the stacked direction of the layers.

The blood flow path layer 21 has a blood flow path through which blood flows and the filtrate flow path layer 31 has a filtrate flow path through which filtrate flows. In the main body portion 2, the blood flow path layer 21 and the filtrate flow path layer 31 are disposed such that the blood flow path and the filtrate flow path face each other with the filtration membrane 41 interposed therebetween. While flowing through the blood flow path, the blood is filtered by the filtration membrane 41, and hazardous substances and unnecessary water in the blood flow into the filtrate flow path and are discharged as filtrate from the filtrate outlet 5. The blood flow path and the filtrate flow path each include at least one fold-back portion therein.

<Configuration of the Blood Flow Path Layer>

Figure 3:
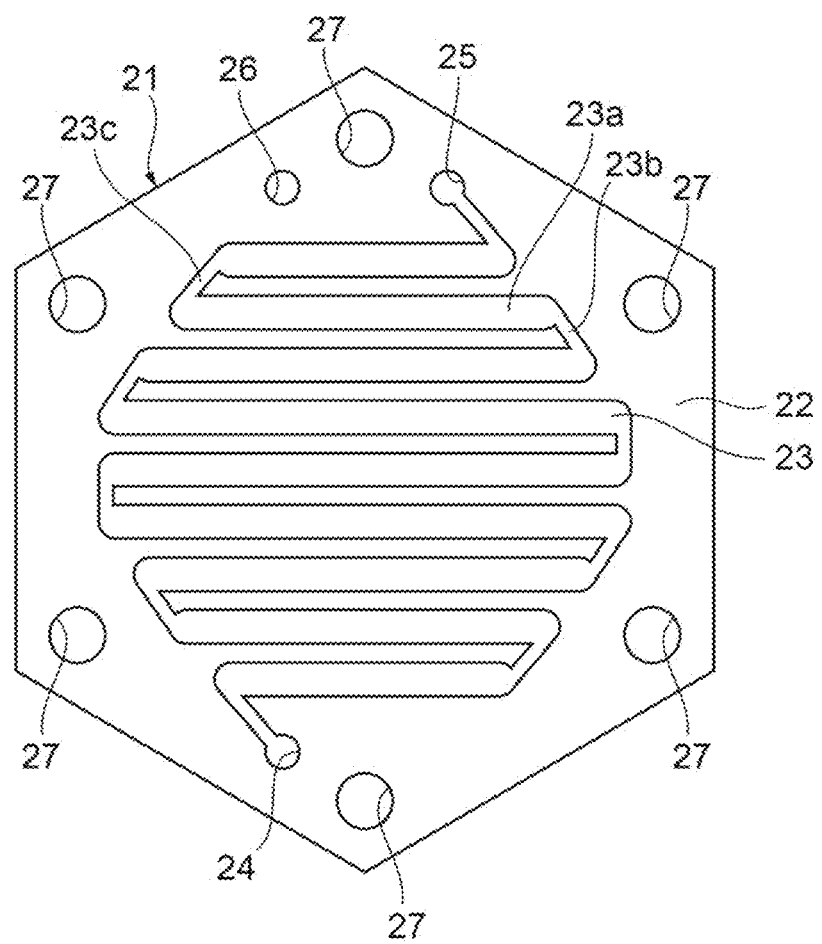
FIG. 3 is a view illustrating a specific example of a blood flow path layer.

FIG. 3 is a view illustrating a specific example of the blood flow path layer.

The blood flow path layer 21 is formed of a thin plate member 22. The plate member 22 may be made of metal material, such as titanium and stainless steel (SUS316L), synthetic resin material, such as plastic, and ceramic material, such as silicone and glass. In the present embodiment, the plate member 22 is formed of a metal plate of titanium with excellent biocompatibility. The plate member 22 has a regular hexagonal shape, and the corner portions of the plate member are each provided with a bolt hole 27 for inserting the bolt 6 therethrough. Further, the plate member 22 is provided with a slot 23 that serves as the blood flow path.

The slot 23 has a zigzag shape in which a plurality of straight portions arranged in parallel to one another with fold-back portions. The slot 23 is covered with the filtration membranes 41 on opposite sides thereof in the stacked direction of the layers in the main body portion 2. One end of the slot 23 is provided with a blood flow-in portion 24 that is in communication with the blood inlet 3 and is continuous in the stacked direction of the layers in the main body portion 2, while the other end of the slot 23 is provided with a blood flow-out portion 25 that is in communication with the blood outlet 4 and is continuous in the stacked direction of the layers in the main body portion 2.

The configuration of the slot 23 will be further described in detail. The slot 23 has a plurality of straight portions 23a that are in parallel to one another, one-ends connecting portions 23b, and the other-ends connecting portions 23c. Each of the one-ends connecting portions 23b connects one ends of adjacent straight portions 23a and each of the other-ends connecting portions 23c connects the other ends of the adjacent straight portions 23a. The one-ends connecting portions 23b and the other-ends connecting portions 23c are alternately and continuously provided as fold-back portions.

In order to secure a longer length of a portion where the blood is filtered within the limited area of the regular hexagonal plate member 22, the plurality of the straight portions 23a arranged in parallel are provided such that those disposed near the center of the plate member 22 are made longer than those disposed near the outer side of the plate member 22. The width and length of the slot 23 are determined on the basis of the amount of blood flow, the blood pressure, and the like.

For example, when the hemofiltration device 1 is directed to be implanted in a human body, the width of the flow path is preferably 0.01 mm to 1 cm, inclusive, and may be 0.1 to 5 mm, inclusive or 0.5 to 4 mm, inclusive. The thickness of the flow path is appropriately adjusted in accordance with the thickness of the device and the number of the stacked layers. However, an excessively thick flow path will accelerate the blood flow rate too much, while a too thin flow path will cause accumulation of impurities as well as stagnation of blood, thereby increasing a risk of clogging of the flow path. From this point of view, the thickness of the flow path is preferably 0.01 mm to 1 cm, inclusive, and may be 0.05 to 5 mm, inclusive or 0.1 to 3 mm, inclusive.

Further, the total area of the flow path is important for obtaining a proper hemofiltration device. The total area of the flow path is preferably 1 to 100,000 $cm^2$, inclusive, and may be 2 to 10,000 $cm^2$, inclusive or 10 to 5,000 $cm^2$, inclusive.

Each of the one-ends connecting portions 23b and the other-ends connecting portions 23c, which are the fold-back portions of the blood flow path, has a curved shape in which the radius of curvature of the wall surface on the outer periphery side of the flow path is larger than that on the inner periphery side of the flow path. This can prevent generation of a portion where the blood locally stagnates in the blood flow path and thus allows the blood to smoothly circulate. Accordingly, the amount of the blood or blood components to be stuck to the wall surfaces of the flow path can be reduced and biofouling can thus be suppressed. The slot width of each of the one-ends connecting portions 23b and the other-ends connecting portions 23c is narrower than that of each of the straight portions 23a, which are portions other than the fold-back portions, and the area where the filtration membrane 41 is exposed in each of the one-ends connecting portions 23b and the other-ends connecting portions 23c is narrower than that in each of the straight portions 23a. With this configuration, when the main body portion 2 is compressed in the stacked direction of the layers, clogging of the slot 23 caused by the filtration membrane 41 that has deformed and thus projected into either the one-ends connecting portions 23b or the other-ends connecting portions 23c is prevented, so that a sufficient amount of the blood flow can be secured.

The slot 23 is produced through, for example, wire electro-discharge machining, and may also be subjected to mechanical polishing using a micro grinder and mirror polishing using electrolytic etching. Through the mechanical polishing, layers that have been thermally and electrolytically altered by the wire electro-discharge machining can be removed, and with the electrolytic etching, a passivation film can be formed on the surface of the wall surface of the flow path. This can reduce the surface roughness of the wall surface of the flow path. Methods for forming the slot 23 on the plate member 22 and for reducing the surface roughness of the wall surface of the flow path of the slot 23 can be appropriately selected from publicly known methods in accordance with the material, machining accuracy, manufacturing cost, and the like of the plate member 22.

The slot 23 may have a problem specific to implantable hemofiltration devices that when the wall surface of the flow path is too rough, the blood or blood components adhere thereto, while when the wall surface of the flow path is too smooth, the blood flow rate becomes too high, thereby lowering the filtration efficiency. From this point of view, when the surface roughness of the wall surface of the flow path is measured in an area of a 50 μm square, it is preferable that the maximum height Rz defined by JIS B 0601:2001 is 0.01 to 10 μm, inclusive or the arithmetic average roughness Ra defined by JIS B 0601:2001 is 0.01 to 3 μm, inclusive, and Rz may be 0.1 to 10 μm, inclusive or Ra may be 0.05 to 3 μm, inclusive; Rz may be 0.5 to 5 μm, inclusive or Ra may be 0.1 to 1 μm, inclusive; or Rz may be 1 to 5 μm, inclusive or Ra may be 0.1 to 0.8 μm, inclusive.

Further, when the blood flow path layer 21 and the filtrate flow path layer 31 form a stacked structure, the slots of the layers may have the same level of surface roughness of the wall surface of the flow path or may be adjusted such that the slots on the side of the second end plate 61 have smaller surface roughness of the wall surface of the flow path than that on the other side.

Furthermore, the plate member 22 is provided with a filtrate passing hole 26. The filtrate passing hole 26 is provided at a position to be disposed continuously with a filtrate flow-out portion 36 of a plate member 32 of the filtrate flow path layer 31 in the stacked direction of the layers in the main body portion 2.

The filtrate passing hole 26 is disposed at a position closer to the blood flow-out portion 25 than to the blood flow-in portion 24 of the slot 23. That is, the distance between the blood flow-in portion 24 and the filtrate passing hole 26 is longer than that between the blood flow-out portion 25 and the filtrate passing hole 26. In the blood flow path, the blood pressure is the highest in the vicinity of the blood flow-in portion 24, and therefore, when the distance between the blood flow-in portion 24 and the filtrate passing hole 26 is short, the blood is likely to move toward the filtrate flow path through the gap between the filtration membrane and the blood flow path layer 21 and be then mixed into the filtrate. In contrast, in the present embodiment, since the distance between the blood flow-in portion 24 and the filtrate passing hole 26 is secured to be long, the blood can be prevented from being mixed into the filtrate, thereby making it possible to stably collect filtrate.

<Configuration of the Filtrate Flow Path Layer>

Figure 4:
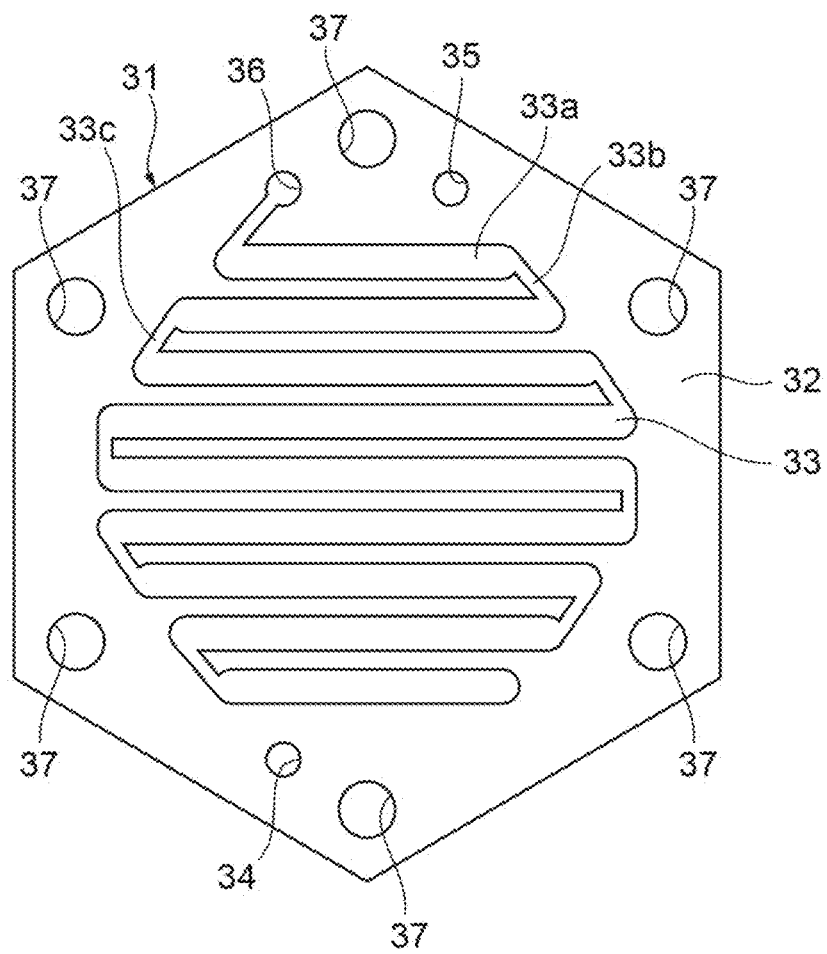
FIG. 4 is a view illustrating a specific example of a filtrate flow path layer.

FIG. 4 is a view illustrating a specific example of the filtrate flow path layer.

The filtrate flow path layer 31 is formed of a thin plate member 32. The plate member 32 may be made of metal material, such as titanium and stainless steel (SUS316L), synthetic resin material, such as plastic, and ceramic material, such as silicone and glass. In the present embodiment, the plate member 32 is formed of the same titanium metal plate as that of the plate member 22 of the blood flow path layer 21. The plate member 32 has a regular hexagonal shape with the same size as that of the plate member 22 of the blood flow path layer 21, and the corner portions of the plate member are each provided with a bolt hole 37 for inserting the bolt 6 therethrough. Each of the bolt holes 37 has the same size as that of the bolt hole 27 of the plate member 22 of the blood flow path layer 21, and the bolt hole 37 is disposed at a position coaxial and continuous with the bolt hole 27 in the main body portion 2.

Further, the plate member 32 is provided with a slot 33 for forming the filtrate flow path. The slot 33 has a zigzag shape in which a plurality of straight portions arranged in parallel to one another with fold-back portions. The slot 33 is covered with the filtration membranes 41 on opposite sides thereof in the stacked direction of the layers in the main body portion 2. The slot 33 at least partially overlaps the slot 23 of the blood flow path layer 21, with the filtration membrane 41 interposed therebetween, in the stacked direction of the layers in the main body portion 2. Accordingly, the blood flowing through the slot 23 of the blood flow path layer 21 is filtered by the filtration membrane 41 in the portions where the slots overlap each other, and thus the filtrate can be made to flow into the filtrate flow path formed by the slot 33.

One end of the slot 33 is provided with the filtrate flow-out portion 36. The filtrate flow-out portion 36 is disposed at a position continuous with the filtrate passing hole 26 of the blood flow path layer 21 in the stacked direction of the layers in the main body portion 2, and communicates with the filtrate outlet 5. With this configuration, the filtrate that has passed through the slot 33 of the filtrate flow path flows from the filtrate flow-out portion 36 into the filtrate outlet 5 and is then discharged to the outside of the main body portion 2.

The configuration of the slot 33 will be further described in detail. The slot 33 has a plurality of straight portions 33a that are in parallel to one another, one-ends connecting portions 33b, and the other-ends connecting portions 33c. Each of the one-ends connecting portions 33b connects one ends of adjacent straight portions 33a and each of the other-ends connecting portions 33c connects the other ends of the adjacent straight portions 33a. The one-ends connecting portions 33b and the other-ends connecting portions 33c are alternately and continuously provided as fold-back portions.

The straight portions 33a are provided at positions to overlap the straight portions 23a of the slot 23 of the plate member 22 of the blood flow path layer 21 in the stacked direction of the layers in the main body portion 2, and each of the straight portions 33a has the same shape as that of each of the straight portions 23a that they overlap. Similarly to the straight portions 23a of the blood flow path layer 21, the plurality of the straight portions 33a arranged in parallel are provided such that those disposed near the center of the plate member 32 are longer than those disposed near the outer side of the plate member 32. Similarly to the one-ends connecting portions 23b and the other-ends connecting portions 23c of the blood flow path layer 21, each of the one-ends connecting portions 33b and the other-ends connecting portions 33c has a curved shape in which the radius of curvature of the wall surface on the outer periphery side of the flow path is larger than that on the inner periphery side of the flow path. This can prevent generation of a portion where the filtrate locally stagnates in the filtrate flow path and thus allows the filtrate to circulate smoothly and be guided to the filtrate flow-out portion 36.

The slot 33 is produced through, for example, wire electro-discharge machining, and similarly to the slot 23 of the blood flow path layer 21, may also be subjected to mechanical polishing using a micro grinder and mirror polishing using electrolytic etching. Through the mechanical polishing, layers that have been thermally and electrolytically altered by the wire electro-discharge machining can be removed, and with the electrolytic etching, a passivation film can be formed on the surface of the wall surface of the flow path. This can reduce the surface roughness of the wall surface of the flow path of the slot 33. Methods for forming the slot 33 on the plate member 32 and for reducing the surface roughness of the wall surface of the flow path of the slot 33 can be appropriately selected from publicly-known methods in accordance with the material, machining accuracy, manufacturing cost, and the like of the plate member 32.

When the surface roughness of the wall surface of the flow path is measured in an area of a 50 µm square, it is preferable that the maximum height Rz defined by JIS B 0601:2001 is 0.01 to 10 µm, inclusive or the arithmetic average roughness Ra defined by JIS B 0601:2001 is 0.01 to 3 µm inclusive, and Rz may be 0.1 to 10 µm, inclusive or Ra may be 0.05 to 3 µm, inclusive; Rz may be 0.5 to 5 µm, inclusive or Ra may be 0.1 to 1 µm, inclusive; or Rz may be 1 to 5 µm, inclusive or Ra may be 0.1 to 0.8 µm, inclusive.

Further, the plate member 32 is provided with blood passing holes 34 and 35. The blood passing holes 34 and 35 are provided at positions to be disposed continuously with the blood flow-in portion 24 and blood flow-out portion 25 of the plate member 22 of the blood flow path layer 21, respectively, in the stacked direction of the layers in the main body portion 2.

<Configuration of the Filtration Membrane>

Figure 5:
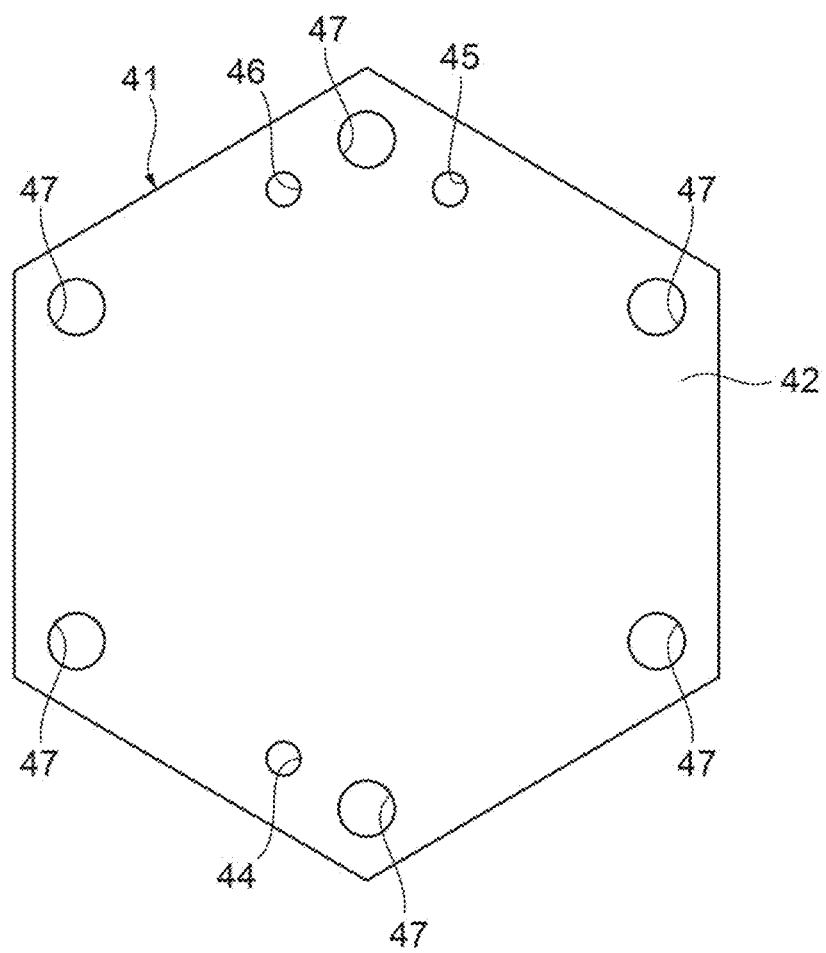
FIG. 5 is a view illustrating a specific example of a filtration membrane.

FIG. 5 is a view illustrating a specific example of the filtration membrane.

The filtration membrane 41 is adapted to filter the blood so as to remove hazardous substances and unnecessary water from the blood. The filtration membrane 41 is formed of a polymer membrane having many nanoscale pores. In the present embodiment, PES (polyethersulfone) membrane is used. The PES membrane can selectively filter only blood components having a low molecular weight through the nanoscale pores and take out hazardous substances and unnecessary water from the blood.

The PES that forms the filtration membrane 41 is described in, for example, JOURNAL OF MICROELECTROMECHANICAL SYSTEMS, Vol. 21, No. 6, December 2012, pp. 1288-1290, Materials 2013, 6, 4309-4323. For the filtration membrane of the present invention, any publicly-known filtration membrane may be appropriately adopted in consideration of the size of the molecules to be targeted for removal. Further, when the device has a plurality of filtrate flow path layers 31 therein, all of the filtrate flow path layers 31 may be made of the same material, or the material of each of the filtrate flow path layers 31 may be adjusted in consideration of the blood pressure or blood flow rate in each of the filtrate flow path layers 31. Examples of the publicly-known filtration membranes may include membranes of low-molecular-weight polysulfone (for example, JP H4-338224 A and JP H11-309355 A) and those of high-molecular-weight polysulfone (JP H9-70524 A), and membranes of polyamide, polyethylene, and polymethylmethacrylate.

The filtration membrane 41 may be subjected to surface treatment, such as deposition of a thin film like a diamond-like carbon film, and application of a fluorine-based polymer. With the surface treatment applied to the filtration membrane 41, the amount of blood or blood components to be stuck to the surface of the filtration membrane 41 can be reduced and biofouling can thus be suppressed.

The filtration membrane 41 has a regular hexagonal shape with the same size as that of the plate member 22 of the blood flow path layer 21, and the corner portions of the filtration membrane 41 are each provided with a bolt hole 47 for inserting the bolt 6 therethrough. Each of the bolt holes 47 has the same size as that of the bolt hole 27 of the plate member 22 of the blood flow path layer 21, and the bolt hole 47 is disposed at a position coaxial and continuous with the bolt hole 27 in the main body portion 2.

Figure 8:
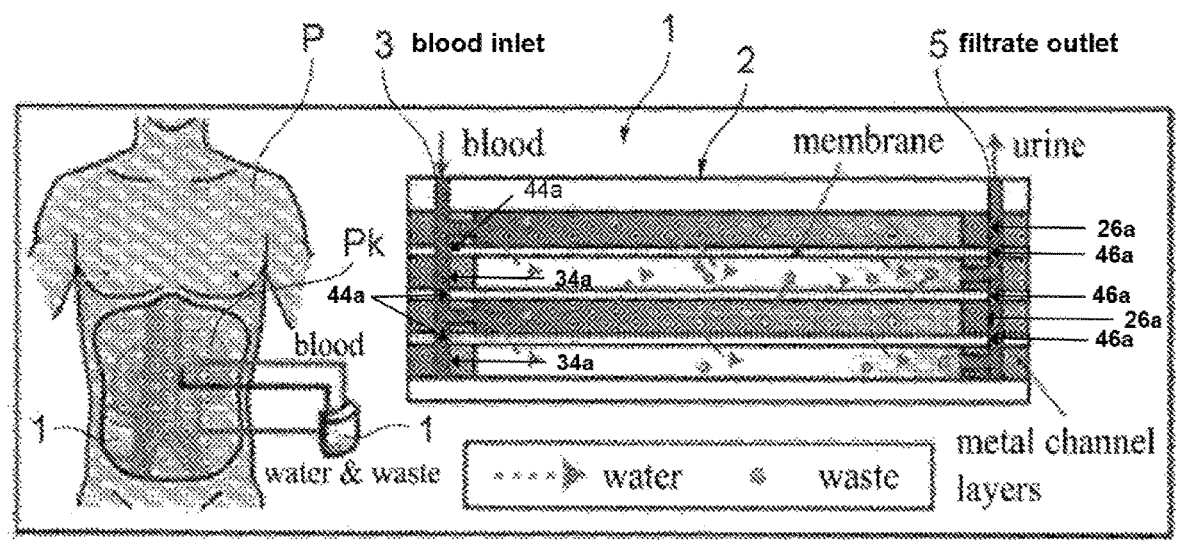
FIG. 8 is a diagram conceptually illustrating a hemofiltration device in a mounted state of an embodiment.

The filtration membrane 41 is further provided with blood passing holes 44 and 45 and a filtrate passing hole 46. The blood passing holes 44 and 45 are provided such that the blood passing hole 44 is disposed at a position continuous with the blood flow-in portion 24 of the plate member 22 of the blood flow path layer 21 and the blood passing hole 34 of the plate member 32 of the filtrate flow path layer 31, and the blood passing hole 45 is disposed at a position continuous with the blood flow-out portion 25 of the plate member 22 of the blood flow path layer 21 and the blood passing hole 35 of the plate member 32 of the filtrate flow path layer 31 in the stacked direction of the layers in the main body portion 2. As shown in FIG. 8, the blood passing holes 34 and 44 form a portion of a blood inlet 3. In other words, the blood inlet 3 includes a first cross section 34a of the filtrate flow path layer 31 and a first cross section 44a of the filtration membrane 41. Likewise, the blood passing holes 35 and 45 form a portion of a blood outlet 4 (not shown in FIG. 8). In other words, the blood outlet 4 includes a third cross section of the filtrate flow path layer 31 and a third cross section of the filtration membrane 41.

The filtrate passing hole 46 is provided at a position to be disposed continuously with the filtrate flow-out portion 36 of the plate member 32 of the filtrate flow path layer 31 and the filtrate passing hole 26 of the plate member 22 of the blood flow path layer 21 in the stacked direction of the layers in the main body portion 2. The filtration membrane 41 is interposed between the blood flow path layer 21 and the filtrate flow path layer 31 in the main body portion 2, and filters the blood passing through the blood flow path of the blood flow path layer 21 and then discharges the filtrate to the filtrate flow path of the filtrate flow path layer 31. As shown in FIG. 8, the filtrate passing holes 26 and 46 form a portion of a filtrate outlet 5. In other words, the filtrate outlet 5 includes a second cross section 26a of the blood flow path layer 21 and a second cross section 46a of the filtration membrane 41.

<Configuration of the End Plate>

Figure 6:
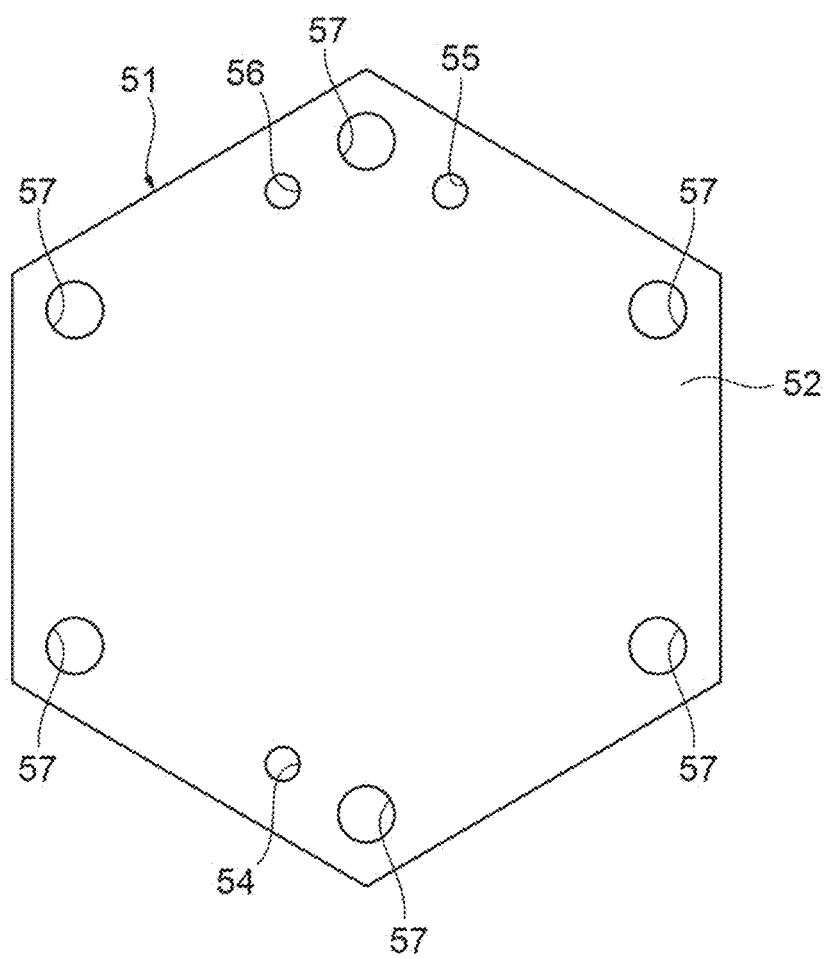
FIG. 6 is a view illustrating a specific example of a first end plate.
Figure 7:
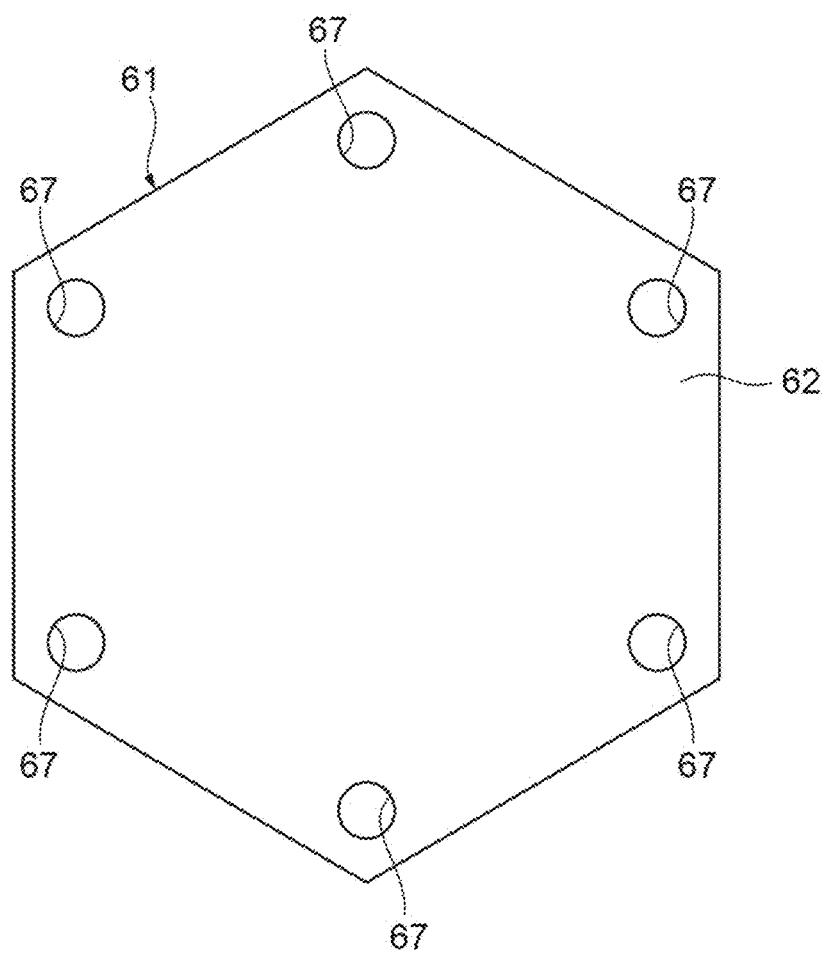
FIG. 7 is a view illustrating a specific example of a second end plate.

FIGS. 6 and 7 are views illustrating specific examples of the first end plate and the second end plate, respectively.

The first end plate 51 and the second end plate 61 are respectively formed of plate members 52 and 62 that are thicker than each of the blood flow path layer 21, filtrate flow path layer 31, and filtration membrane 41. The plate members 52 and 62 are required to have rigidity to such an extent that they can hold the blood flow path layer 21, filtrate flow path layer 31, and filtration membrane 41, from opposite sides in the stacked direction of the layers, with a uniform holding force and with small deflection. In the present embodiment, plate members made of synthetic resin material are used for reasons, for example, that the synthetic resin material is lightweight and is easily processed. Specifically, an acrylic plate that has a predetermined plate thickness is used for each of the plate members of the present embodiment.

The plate members 52 and 62 each have a regular hexagonal shape with the same size as that of the plate member 22 of the blood flow path layer 21, and the corner portions of the plate members 52 and 62 are provided with bolt holes 57 and 67, respectively, for inserting the bolts 6 therethrough. Since the plate members 52 and 62 each have a regular hexagonal shape, a total of six bolt holes 57 are equidistantly positioned with a central angle of 60° between adjacent bolt holes 57, and a total of six bolt holes 67 are positioned similarly to the bolt holes 57.

Therefore, as compared to the configuration of an end plate that has a square outline and has bolt holes on the four corner portions thereof, for example, in the end plate having a regular hexagonal outline of the present embodiment, the intervals between adjacent bolts 6 can be made narrower and more number of bolts 6 can be disposed. With this configuration, the first end plate 51 and second end plate 61 can be uniformly compressed with a high pressure in the stacked direction of the layers, and thus leakage of the blood and the filtrate from the blood flow path and the filtrate flow path to the outside of the main body portion 2 can be prevented.

Of the plate member 52 of the first end plate 51 and the plate member 62 of the second end plate 61, only the plate member 52 is provided with blood passing holes 54 and 55 and a filtrate passing hole 56. Thus, the hemofiltration device 1 has a configuration in which the blood inlet 3, blood outlet 4, and filtrate outlet 5 are provided on one side of the main body portion 2 in the stacked direction of the layers (see FIG. 1).

<Method of Use>

Figure 9A:
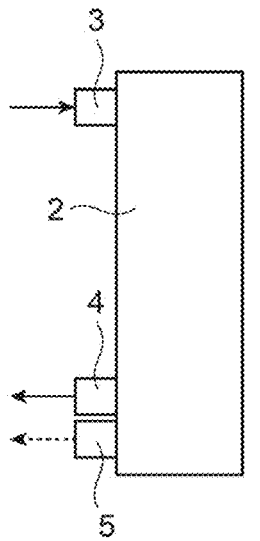
FIGS. 9A and 9B are views illustrating specific examples of the configuration of a hemofiltration device in a mounted state of an embodiment.
Figure 9B:
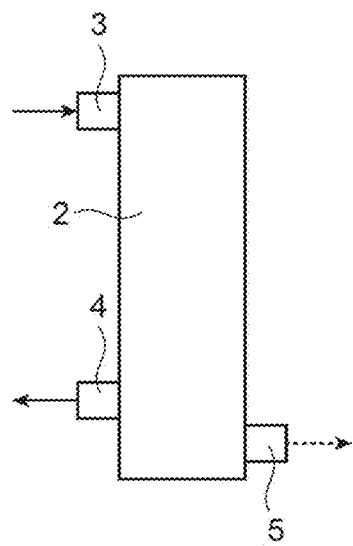

FIG. 8 is a diagram conceptually illustrating the hemofiltration device in a mounted state of the present embodiment and FIGS. 9A and 9B are views illustrating specific examples of the configuration of the hemofiltration device in a mounted state of the present embodiment.

As shown in FIG. 8, the hemofiltration device 1 is used by being implanted in a body of a mammal P, such as a human. The blood inlet 3 and the blood outlet 4 are bypass-connected to the blood vessels on the upstream side of the kidney Pk, and the filtrate outlet 5 is connected to the ureter that extends from the kidney Pk. Their connections to the blood vessels and ureter are made by means of flexible tubes (not shown).

In the hemofiltration device 1, the blood is made to flow into the main body portion 2 from the blood inlet 3, pass through the blood flow path of the blood flow path layer 21, and then flow out from the blood outlet 4. Further, while passing through the blood flow path, the blood is filtered by the filtration membrane 41 so that hazardous substances and unnecessary water are taken out from the blood to the filtrate flow path of the filtrate flow path layer 31 and discharged as filtrate from the filtrate outlet 5, and then poured into the ureter or directly taken out to the outside of the body.

As shown in FIG. 9A, in the present embodiment, the blood inlet 3, blood outlet 4, and filtrate outlet 5 are provided on one side of the main body portion 2 in the stacked direction of the layers. However, when the hemofiltration device 1 is considered to be implanted in, for example, the abdomen of a dog, it is more efficient to provide the blood inlet 3 and blood outlet 4 on one side and provide the filtrate outlet 5 on the other side in the stacked direction of the layers so that they face opposite directions, as shown in FIG. 9B.

In this case, with the use of the first end plate 51 that has no filtrate passing hole 56 provided on the plate member 52 thereof and the second end plate 61 that has the filtrate passing hole provided on the plate member 62 thereof, it is possible to dispose the blood inlet 3 and blood outlet 4 on one side of the main body portion 2 in the stacked direction of the layers and dispose the filtrate outlet 5 on the other side, that is, the filtrate outlet 5 can face the direction opposite to the direction that the blood inlet 3 and blood outlet 4 face.

According to the hemofiltration device 1 of the present embodiment, with changes to the configurations of the plate member 52 of the first end plate 51 and the plate member 62 of the second end plate 61, the sides on which the blood inlet 3, blood outlet 4, and filtrate outlet 5 are disposed in the stacked direction of the layers can be easily switched. Therefore, when the hemofiltration device 1 of the present embodiment is implanted and mounted in a mammalian body, the blood inlet 3, blood outlet 4, and filtrate outlet 5 can be selectively disposed, on either the same side or different sides in the stacked direction of the layers in accordance with the position and orientation of the device and how to take out the filtrate.

<Functions and Effects>

According to the aforementioned hemofiltration device 1 of the present embodiment, since the filtrate outlet 5 of the filtrate flow path is provided at a position closer to the blood outlet 4 than to the blood inlet 3 of the blood flow path, the blood in the blood flow path can be prevented from leaking and being mixed into the filtrate in the filtrate flow path.

In the hemofiltration device 1, in accordance with the location where the hemofiltration device 1 is implanted and how the filtrate is taken out (whether the filtrate is made to flow into the bladder or is directly discharged to the outside of the body), the blood inlet 3, blood outlet 4, and filtrate outlet 5 can be selectively disposed, on either one side or different sides in the stacked direction of the layers. Therefore, the tubes connected to the blood flow path and filtrate flow path can be shortened.

Further, the hemofiltration device has three ports, which are the blood inlet 3, blood outlet 4, and filtrate outlet 5. Therefore, as compared to hemodialysis devices that supply and collect dialysate, for example, the number of ports can be reduced by one. Furthermore, with only one filtrate outlet 5, the filtrate can be effectively collected and the amount of the filtrate remaining in the tube connected to the filtrate outlet 5 can also be reduced. In addition, since there is only one port for taking out the filtrate, operations can be conducted with less difficulty when the filtrate outlet is connected to the ureter or the filtrate is directly taken out to the outside of the body.

In the hemofiltration device 1, the main body portion 2 has a regular hexagonal outline and the corner portions thereof are fastened with bolts and nuts. Therefore, as compared to a main body portion having a square outline, for example, the pitch between portions to be fastened can be made smaller and the main body portion 2 can be more uniformly compressed with a higher pressure in the stacked direction of the layers, and thus leakage of the blood and the filtrate from the blood flow path and the filtrate flow path to the outside of the main body portion 2 can be prevented.

It should be noted that the aforementioned embodiment has described an example of the configuration in which only one filtrate outlet 5 is provided, but for the purpose of obtaining the advantageous effect of preventing the blood from being mixed into the filtrate, the hemofiltration device 1 only needs to have a configuration in which the filtrate outlet 5 is disposed away from the blood inlet 3. Therefore, as a modification, for example, filtrate outlets 5 may be provided at two positions away from the blood inlet 3.

Other Specific Examples

Next, with reference to FIGS. 10 to 15, other specific examples of the blood flow path layer 21 and filtrate flow path layer 31 will be described. It should be noted that constituent elements that are the same as those in the aforementioned embodiment are denoted by the same reference numerals, so as to omit the detailed explanation thereof.

The aforementioned embodiment has described the configuration in which the blood flow path and filtrate flow path both have a zigzag shape, but the flow paths only need to have a shape that can secure a long length of the portion where the blood is filtered and may have any other shapes, for example, a tree shape and a circular shape.

Figure 10:
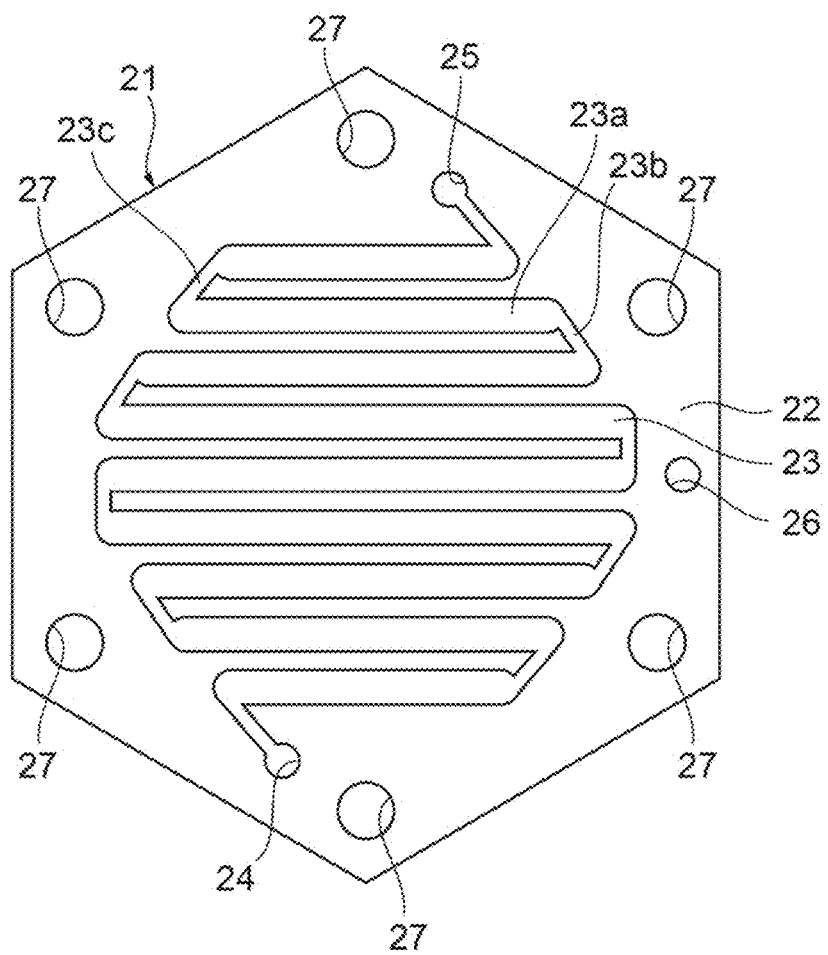
FIG. 10 is a view illustrating another specific example of the blood flow path layer.
Figure 11:
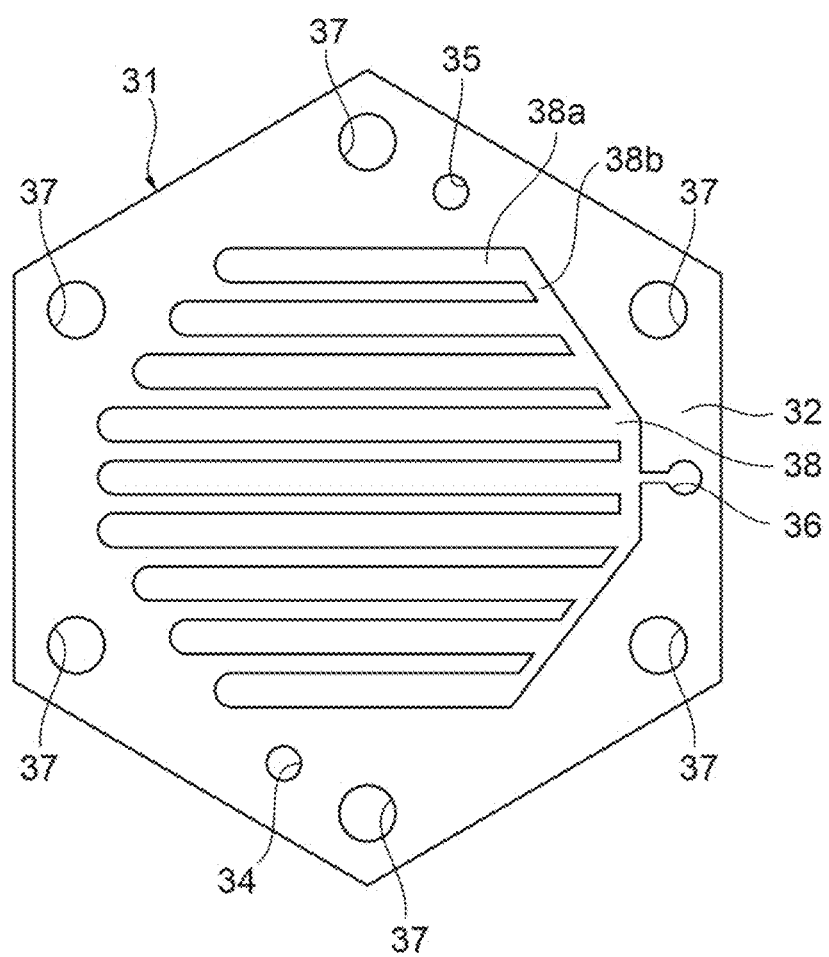
FIG. 11 is a view illustrating another specific example of the filtrate flow path layer.

FIGS. 10 and 11 show a configuration in which the filtrate flow path has a tree shape.

As shown in FIG. 10, the blood flow path layer 21 has the filtrate passing hole 26 disposed near a portion halfway through the flow path of the slot 23. As shown in FIG. 11, the filtrate flow path layer 31 has a slot 38 for forming the filtrate flow path on the plate member 32. The slot 38 has a tree shape in which a plurality of straight portions are arranged in parallel and connected at one ends thereof.

The slot 38 has a plurality of straight portions 38*a* arranged in parallel to one another and a one-ends connecting portion 38*b* that connects adjacent straight portions 38*a* at one ends thereof. The straight portions 38*a* are provided at positions where they overlap the straight portions 23*a* of the slot 23 of the plate member 22 of the blood flow path layer 21 in the stacked direction of the layers in the main body portion 2, and each of the straight portions 38*a* and each of the straight portions 23*a* that overlap each other have the same shape.

The slot 38 is covered with the filtration membranes 41 on opposite sides thereof in the stacked direction of the layers in the main body portion 2. The slot 38 at least partially overlaps the slot 23 of the blood flow path layer 21, with the filtration membrane 41 interposed therebetween, in the stacked direction of the layers in the main body portion 2. Accordingly, the blood passing through the slot 23 of the blood flow path layer 21 is filtered by the filtration membrane 41 in the portions where the slots overlap each other, and thus the filtrate can be made to flow into the filtrate flow path formed by the slot 38.

The filtrate flow-out portion 36 is provided at an end on the side of the one-ends connecting portion 38*b* of the slot 38. The filtrate flow-out portion 36 is disposed at a position continuous with the filtrate passing hole 26 of the blood flow path layer 21 in the stacked direction of the layers in the main body portion 2, and communicates with the filtrate outlet 5. With this configuration, the filtrate that has passed through the slot 38 of the filtrate flow path flows from the filtrate flow-out portion 36 into the filtrate outlet 5 and is then discharged to the outside of the main body portion 2.

Figure 12:
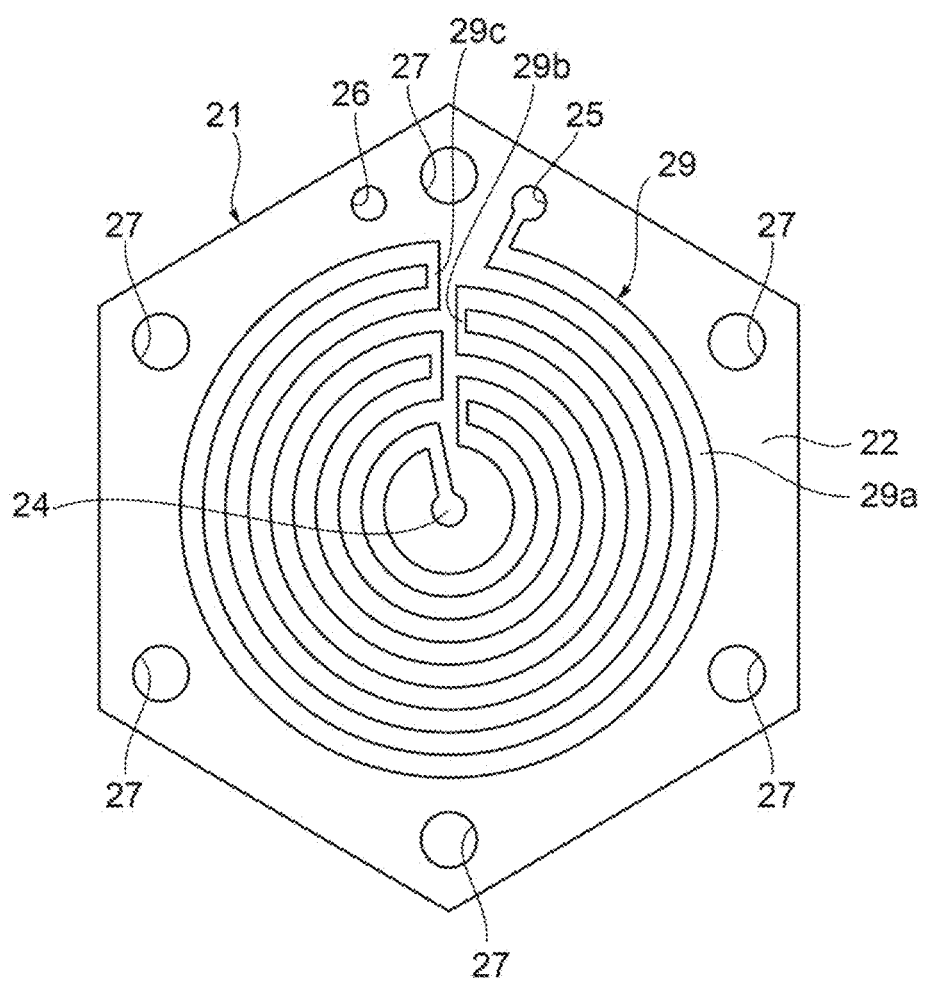
FIG. 12 is a view illustrating yet another specific example of the blood flow path layer.
Figure 13:
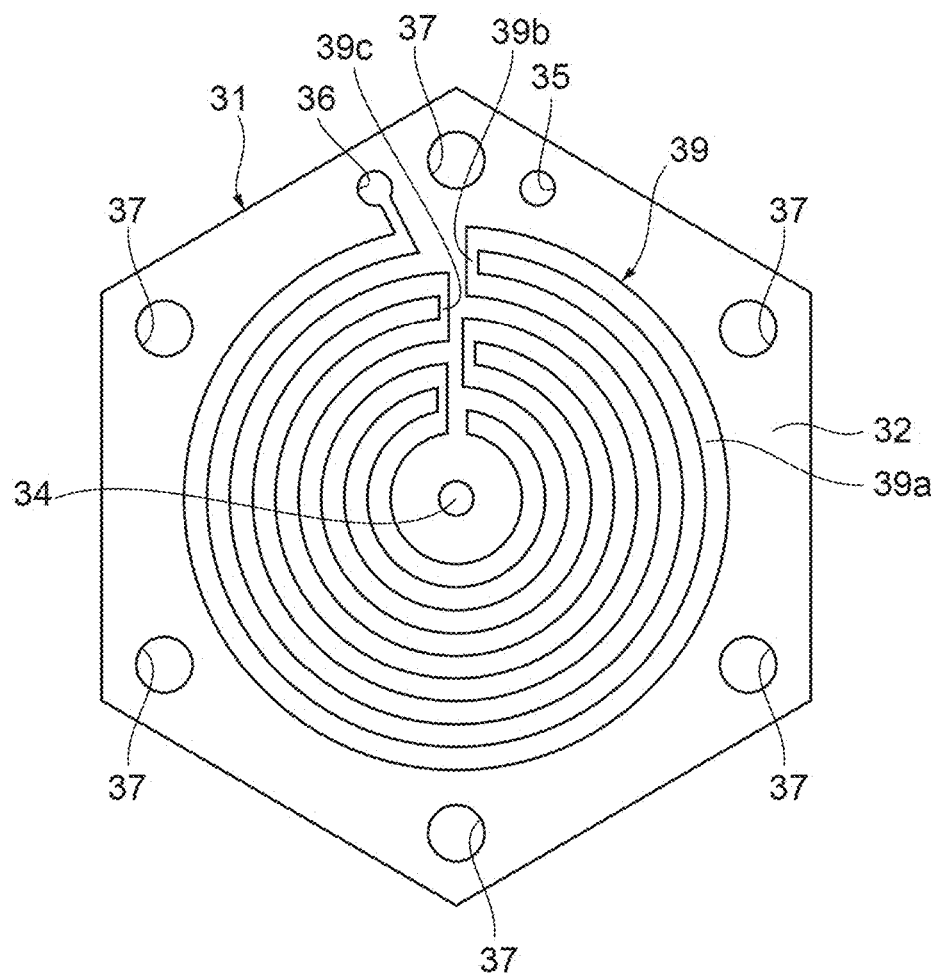
FIG. 13 is a view illustrating yet another specific example of the filtrate flow path layer.

FIGS. 12 and 13 show a configuration in which the filtrate flow path has a circular shape.

The blood flow path layer 21 has a slot 29 for forming the blood flow path on the plate member 22. The slot 29 has a concentric circular shape in which a plurality of substantially circular portions with different diameters, each of which is partially cut out, are concentrically arranged. The slot 29 is covered with the filtration membranes 41 on opposite sides thereof in the stacked direction of the layers in the main body portion 2. One end of the slot 29 is provided with the blood flow-in portion 24 that is continuous in the stacked direction of the layers in the main body portion 2 and communicates with the blood inlet 3. The other end of the slot 29 is provided with the blood flow-out portion 25 that is continuous in the stacked direction of the layers in the main body portion 2 and communicates with the blood outlet 4. The blood flow-in portion 24 is disposed at the center of circular portions 29a, and the blood flow-out portion 25 is disposed radially outward of the circular portions 29a and near the filtrate passing hole 26.

The slot 29 has the substantially circular portions 29a that are in parallel to one another, one-ends connecting portions 29b, and the other-ends connecting portions 29c. Each of the one-ends connecting portions 29b connects one ends of adjacent circular portions 29a and each of the other-ends connecting portions 29c connects the other ends of the adjacent circular portions 29a. The one-ends connecting portions 29b and the other-ends connecting portions 29c are alternately and continuously provided. The width and length of the slot 29 are determined on the basis of the amount of blood flow, the blood pressure, and the like.

The filtrate flow path layer 31 has a slot 39 for forming the filtrate flow path on the plate member 32. The slot 39 has a concentric circular shape in which a plurality of substantially circular portions, each of which is partially cut out, are concentrically arranged. The slot 39 is covered with the filtration membranes 41 on opposite sides thereof in the stacked direction of the layers in the main body portion 2. The slot 39 at least partially overlaps the slot 29 of the blood flow path layer 21 with the filtration membrane 41 interposed therebetween in the stacked direction of the layers in the main body portion 2. Accordingly, the blood passing through the slot 29 of the blood flow path layer 21 is filtered by the filtration membrane 41 in the portions where the slots overlap each other, and thus the filtrate can be made to flow into the filtrate flow path of the slot 39.

The slot 39 has the substantially circular portions 39a that are in parallel to one another, one-ends connecting portions 39b, and the other-ends connecting portions 39c. Each of the one-ends connecting portions 39b connects one ends of adjacent circular portions 39a and each of the other-ends connecting portions 39c connects the other ends of the adjacent circular portions 39a. The one-ends connecting portions 39b and the other-ends connecting portions 39c are alternately and continuously provided. The circular portions 39a are provided at positions where they overlap the circular portions 29a of the slot 29 of the plate member 22 of the blood flow path layer 21 in the stacked direction of the layers in the main body portion 2, and each of the circular portions 29a and each of the circular portions 39a that overlap each other have the same shape.

The blood passing hole 34 is provided at the center of the circular portions 39a. The blood passing hole 34 is disposed at a position continuous with the blood flow-in portion 24 of the blood flow path layer 21 in the stacked direction of the layers in the main body portion 2. One end of the slot 39 is provided with the filtrate flow-out portion 36. The filtrate flow-out portion 36 is disposed at a position continuous with the filtrate passing hole 26 of the blood flow path layer 21 in the stacked direction of the layers in the main body portion 2, and communicates with the filtrate outlet 5. With this configuration, the filtrate that has passed through the slot 39 of the filtrate flow path flows from the filtrate flow-out portion 36 into the filtrate outlet 5 and is then discharged to the outside of the main body portion 2.

Figure 14:
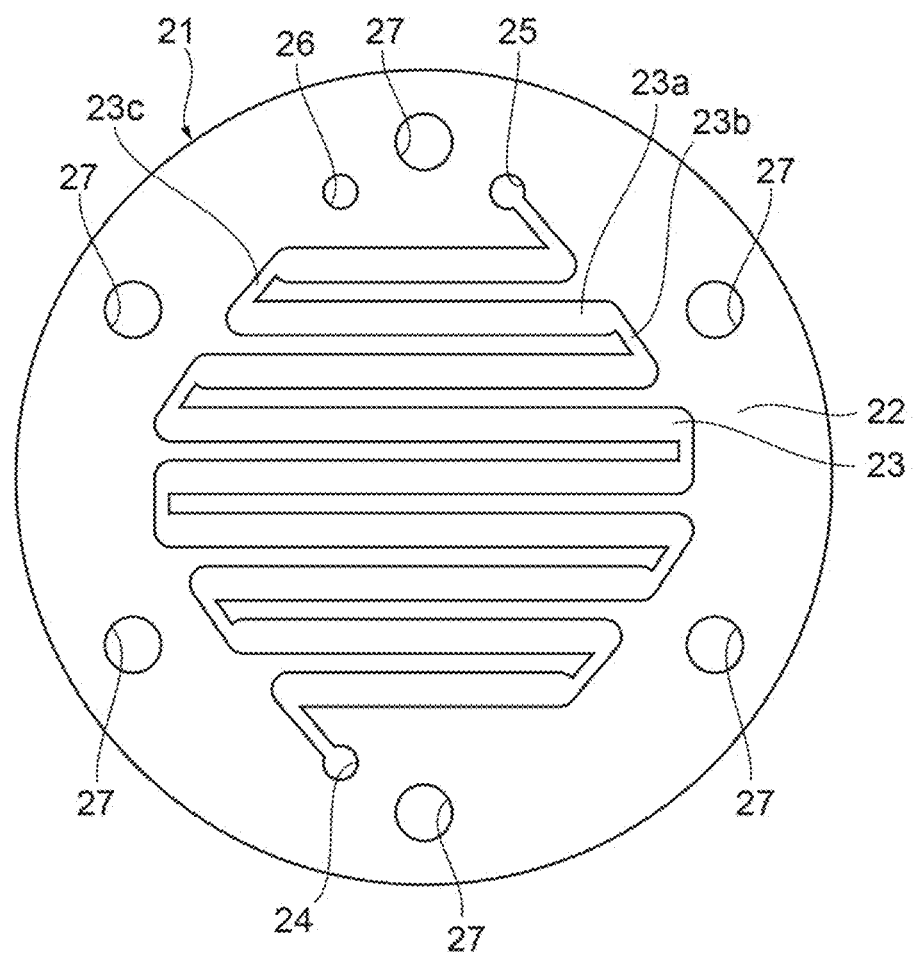
FIG. 14 is a view illustrating still another specific example of the blood flow path layer.
Figure 15:
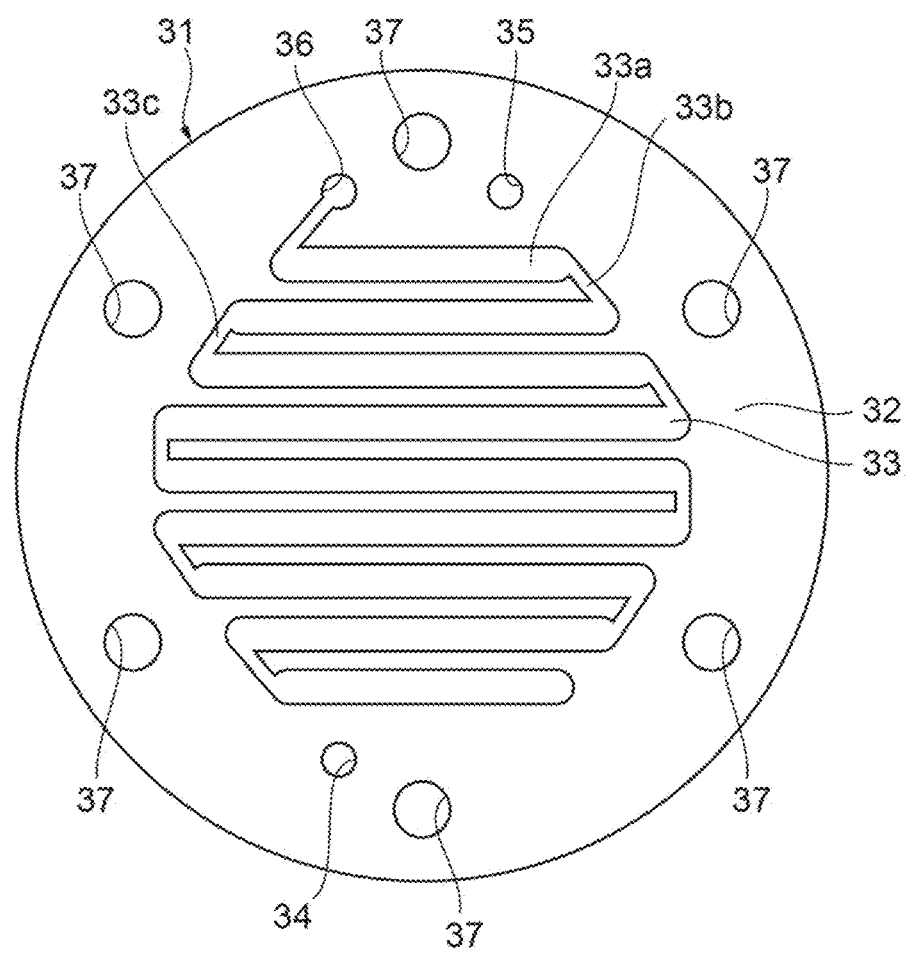
FIG. 15 is a view illustrating still another specific example of the filtrate flow path layer.

FIGS. 14 and 15 are views illustrating a configuration of the blood flow path layer 21 and filtrate flow path layer 31 when the main body portion 2 has a circular outline.

The aforementioned embodiment has described the configuration in which the main body portion 2 has a regular hexagonal outline, but the configuration of the main body portion 2 is not limited to this, and the main body portion 2 may have a regular pentagonal or more polygonal outline or a circular outline. When the main body portion 2 has a regular pentagonal or more polygonal outline or a circular outline, the main body portion 2 can be compressed in the stacked direction of the layers, by means of five or more fastening means equidistantly disposed along the outline. Therefore, as compared to the configuration in which the main body portion 2 has a square outline, the intervals between adjacent bolts 6 can be made narrower and more number of bolts 6 can be disposed. With this configuration, the first end plate 51 and second end plate 61 can be uniformly compressed with a high pressure in the stacked direction of the layers, and thus leakage of the blood and the filtrate from the blood flow path and the filtrate flow path to the outside of the main body portion 2 can be prevented. Further, as compared to the main body portion having a square outline, the main body portion 2 having a regular pentagonal or more polygonal outline or a circular outline is more suitably fit in the living body when implanted therein, and has higher biocompatibility. It should be noted that the slots 23 and 33 may each have a concentrically circular shape similarly to the slots 29 and 39 shown in FIGS. 12 and 13 instead of having a zigzag shape as shown in FIGS. 14 and 15.

The outline of the main body portion 2 is not limited to a regular polygonal shape, but may be any polygonal shape. Other examples of the outline of the main body portion 2 may include a square, pentagon, hexagon, octagon, and dodecagon. Further, the main body portion may be tapered and the rim thereof may be chamfered so as not to damage tissue of the living body when the device is implanted therein. The size and thickness of the device may be appropriately adjusted in accordance with the subject in which the device is mounted. Although it is favorable that the main body portion 2 is not too large as it is implanted in the living body, it is not easy to continue proper hemofiltration with a smaller device. From this point of view, when the hemofiltration device 1 is used in a human body, for example, the area (the area within the outer frame) of the main body portion 2 is set to 0.5 to 1,000 $cm^2$, inclusive, and may be set to 1 to 500 $cm^2$, inclusive, 2 to 100 $cm^2$, inclusive, 3 to 75 $cm^2$, inclusive, or 4 to 50 $cm^2$, inclusive.

Considering that the device is implanted in the living body and that blood is circulated inside the device with the use of the blood pressure, it is favorable that the device is not too thick (in terms of the length from the surface of the first end plate 51 to the surface of the second end plate 61). However, if the device is too thin, the numbers of the blood flow path layers 21 and filtrate flow path layers 31 that are stacked are limited. From this point of view, the thickness of the device is set to, for example, 1 mm to 20 cm, inclusive, and may be set to 5 mm to 15 cm, inclusive or 1 to 10 cm, inclusive.

The number of the hemofiltration devices 1 to be implanted in one living body is not limited to one, but a plurality of devices (two or more devices) may be implanted therein. When the plurality of the hemofiltration devices 1 are implanted in the living body, the individual devices may be implanted in different locations. For example, the blood outlet 4 of the hemofiltration device 1 may be connected to the blood inlet 3 of another device 1 so that the plurality of the hemofiltration devices 1 form a tandem connection (the hemofiltration devices 1 are continuously connected).

[1. Experiment]

<1.1> Implantable Micro Dialysis Device

Existing dialysis treatments require a large amount of dialysate and pumps for its delivery, and thus the systems therefor are large. In contrast, the present device does not use dialysate or a pump, so that downsizing thereof was realized. In the dialysis system of the present device, hazardous substances and unnecessary water are removed from the blood through ultrafiltration with the use of the dialysis membrane. For this purpose, as the dialysis membrane, a PES (polyethylene glycol) membrane having numerous nanoscale pores is used. The PES membrane can selectively filter, through the nanoscale pores, only blood components having a low molecular weight. The PES membrane was formed through mixing of dissolved PES, dissolved PEG (polyethylene glycol), and DMAc (1-1-dimetylacetamid) at percentages of 17.5%, 13.3%, and 69.2% and gelatinization of the mixture. This PES membrane and a metal micro flow path designed to be driven with the blood pressure are alternately disposed.

<1.2> Production of a Micro Flow Path for Biofouling Evaluation

Figure 16A:
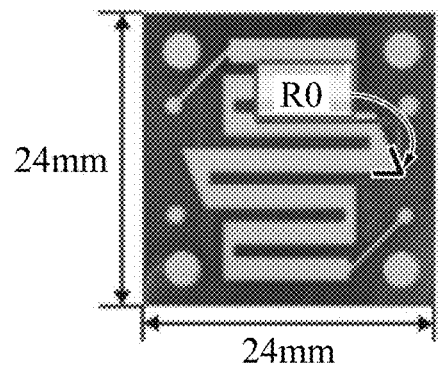
FIGS. 16A to 16C are diagrams illustrating metal flow paths for biofouling evaluation.
Figure 16B:
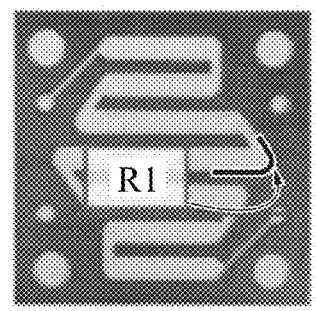
Figure 16C:
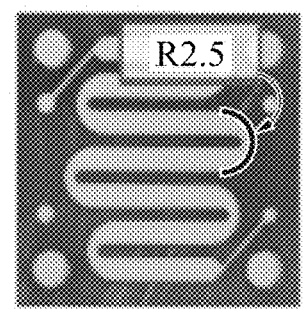

As the material of a metal micro flow path to be mounted in the present implantable dialysis device, highly biocompatible stainless steel SUS316L having a 0.2 mm thickness was used. With the focus, in particular, on the curved portion, which is to be brought into direct contact with the blood, of the micro flow path, micro flow paths were produced through the wire electro-discharge machining. The micro flow paths produced have radii of curvature of 0, 1, and 2.5 mm, respectively, as shown in FIGS. 16A, 16B, and 16C. Then, mechanical polishing using a micro grinder and mirror polishing using electrolytic etching were performed and eight such micro flow paths were produced. Through the mechanical polishing, the layers that have been thermally and electrolytically altered by the wire electro-discharge machining were removed, and with the electrolytic etching, a passivation film was formed on the surface of each of the flow paths. Each of the flow paths and PDMS (polydimethylsiloxane) used for prevention of the leakage were alternately stacked to thereby produce the device for biofouling evaluation without the use of a dialysis membrane.

Figure 17:
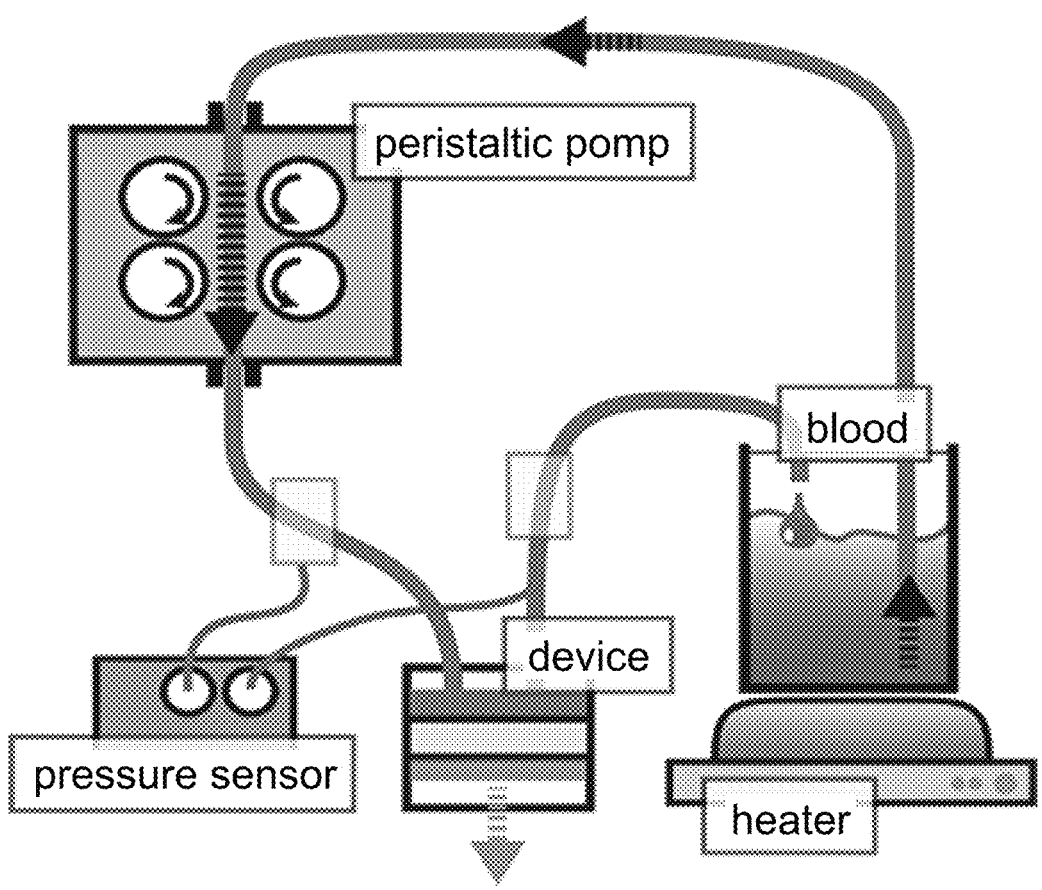
FIG. 17 is a schematic diagram of a circulation circuit.

<1.3> Method of Biofouling Evaluation Experiment of the Wall Surface of the Flow Path As shown in FIG. 17, a circulation circuit that uses a peristaltic pump was prepared so that the whole blood of a human body was circulated through the aforementioned device for seven days. The amount of the flow rate herein was measured and adjusted using a polygraph device so that the average pressure at the blood flow-in portion of the device became 120 mmHg that is the average blood pressure of a human body. The blood was agitated so as not to be separated in a beaker, and the temperature of the dialysate was maintained at 36° C. Immediately after the circulation of the blood for seven days, cells of proteins stuck to the wall surface of the metal flow path were immobilized and the wall surface of the micro flow path was observed using an SEM.

Figure 18A:
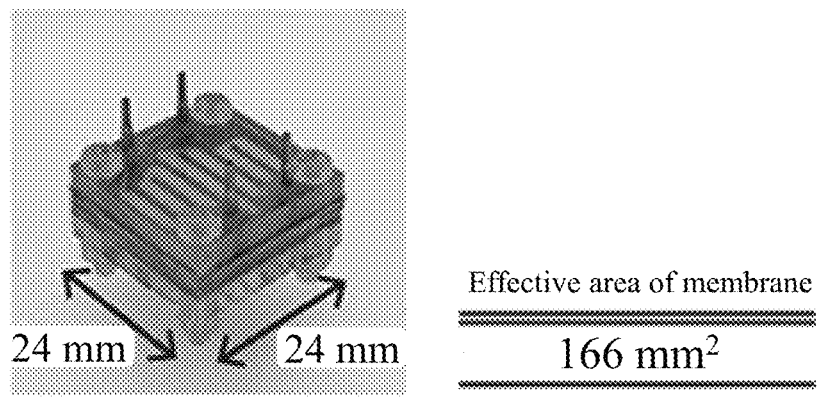
FIGS. 18A to 18E are views illustrating specific examples of a hemofiltration device used for experiment on a medium-sized animal.

<1.4> Designing and Selection of a Dialysis Device for Experiment on a Medium-Sized Animal The device that has been developed in the prior research, as shown in FIG. 18A, has a problem that the effective area of each sheet of dialysis membrane is small and thus an enormous number of layers should be stacked for securing the amount of filtrate equivalent to that of urine of a medium-sized animal. Considering such a problem, the four kinds of devices shown in FIGS. 18B, 18C, 18D, and 18D were produced, each of which has an enlarged effective area of each sheet of dialysis membrane as compared to that of the device developed in the prior research, and the most suitable device among the four was experimentally selected.

<1.5> Experiment of Devices having Different Numbers of Stacked Layers for Experiment on a Medium-Sized Animal and the Evaluation Method thereof For conducting an in vitro evaluation of the device selected in 1.4 above, experiment was conducted for cases in which the device has 3, 9, and 19 dialysis membranes mounted thereon, using the same circulation circuit as that used in the evaluation experiment conducted in 1.3 above, and the whole blood of a human body. It should be noted that the average blood pressure at the blood flow-in portion of the device was set to 110 mmHg that is the average blood pressure of a medium-sized dog body, and that the amount of filtrate was measured every 15 minutes three times in total after the commencement of the experiment. The evaluation of the permeability of the dialysis device is defined as in Formula 1 below using a filtration coefficient Lp.

[Formula 1]

$$L_P = \frac{V_F}{T_F \times TMP \times A} \left[\frac{ml}{h \cdot mmHg \cdot m^2}\right], \quad (1)$$

where $V_F$ [ml], $T_F$ [h], TMP [mmHg], and A [m$^2$] represent the amount of filtrate, the time duration of filtration, the pressure difference between membranes, and the effective area of the membrane, respectively.

[2. Results of the Experiment]

<2.1.> Results of the Biofouling Evaluation Experiment

Figure 19A:
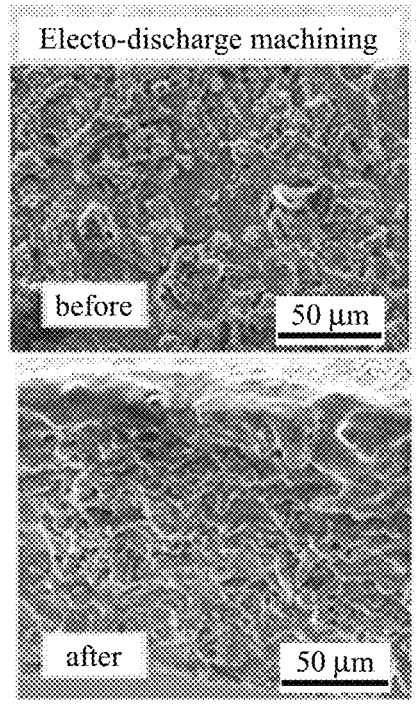
FIGS. 19A to 19C are SEM images of wall surfaces of flow paths.
Figure 19B:
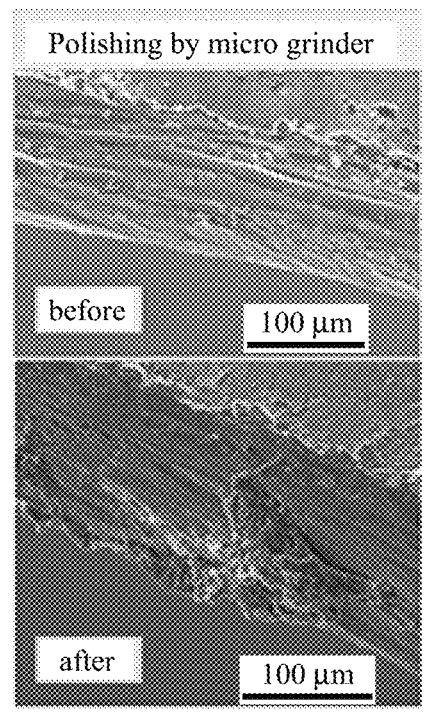
Figure 19C:
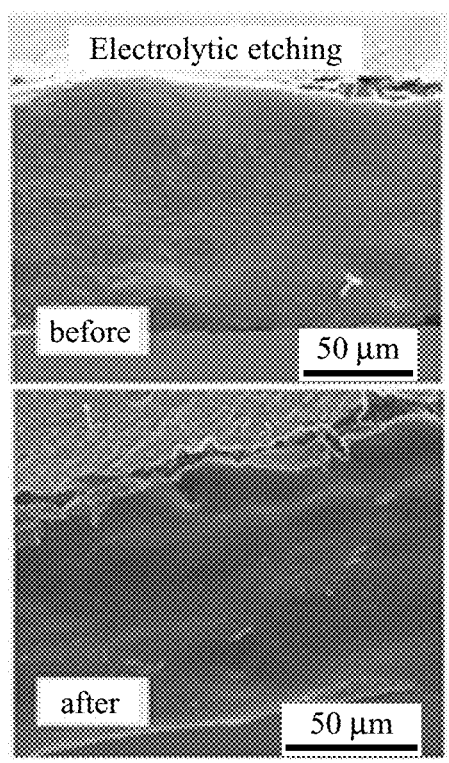

FIGS. 19A to 19C show the surfaces with R2.5 to be machined and SEM images taken after the experiment. On the surface that was subjected to the electro-discharge machining, thermally and electrolytically altered layers were formed and adhesion of the blood and blood components was observed in many spots. The altered layers were removed through the machining using a micro grinder, which was able to reduce the amount of the adhesion. Further, with a passivation film formed using the electrolytic etching, the amount of the adhesion was able to be further substantially reduced. However, when the biofouling evaluation was conducted on the flow paths with different radii of curvature, it was found that with a larger radius of curvature, biofouling was reduced, but the differences observed among the flow paths with different radii of curvature were not as significant as those observed when the flow paths have different surface conditions.

<2.2> Results of Experiment for Selecting a Device for a Medium-Sized Animal

Figure 18B:
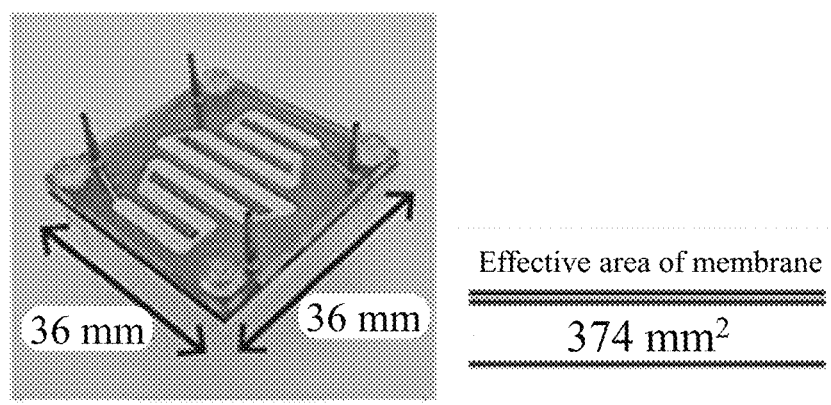
Figure 18C:
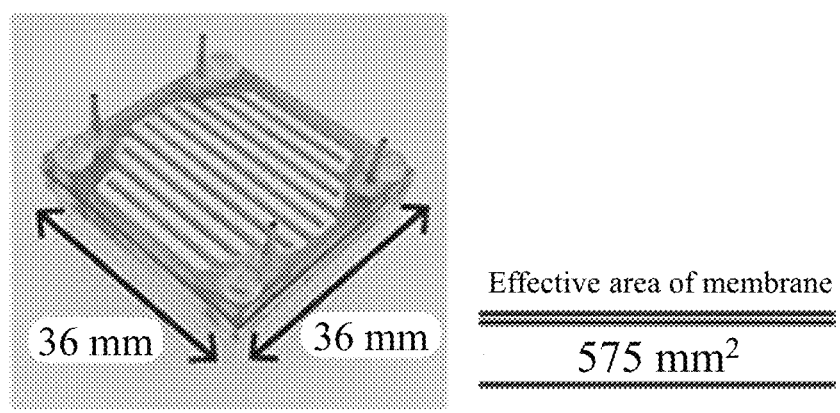
Figure 18D:
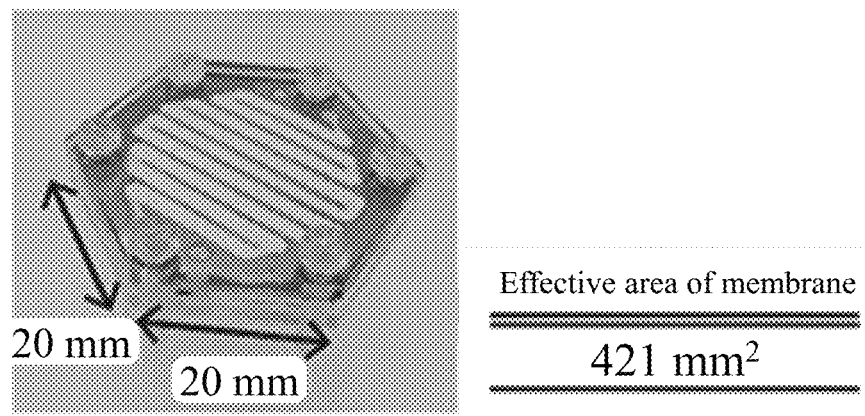

With the devices of FIGS. 18B and 18C, filtrate was not able to be obtained. That was because the width of the flow path of the device of 18B is wide and thus the flow path was clogged due to the PES membrane deflected by the blood pressure. Further, in both of the devices of 18B and 18C, the intervals (36 mm) between screw holes are large and thus the force of sandwiching the PMMA was decreased, thereby causing the blood to leak to the outside through the side surfaces of the devices. With the device of FIG. 18D, filtrate was obtained, but as the blood inlet and the filtrate outlet are disposed close to each other, the blood was mixed into the filtrate. With the device (a product of the present invention) shown in FIG. 18E, filtrate was stably obtained.

Figure 18E:
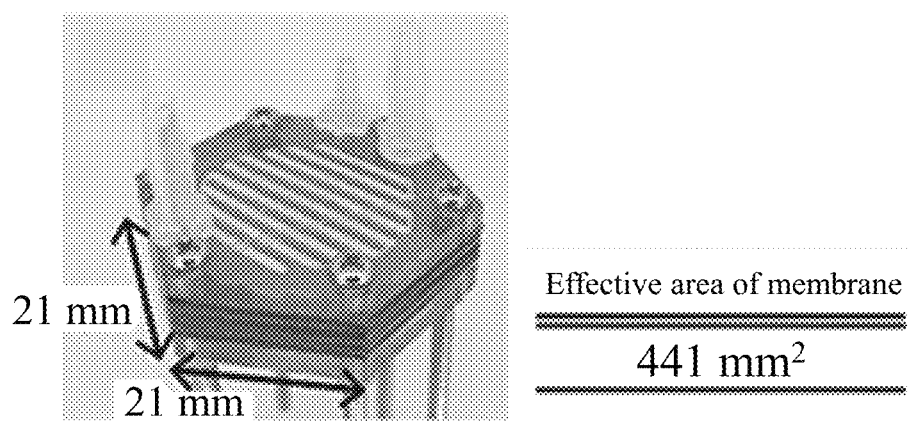
Figure 20:
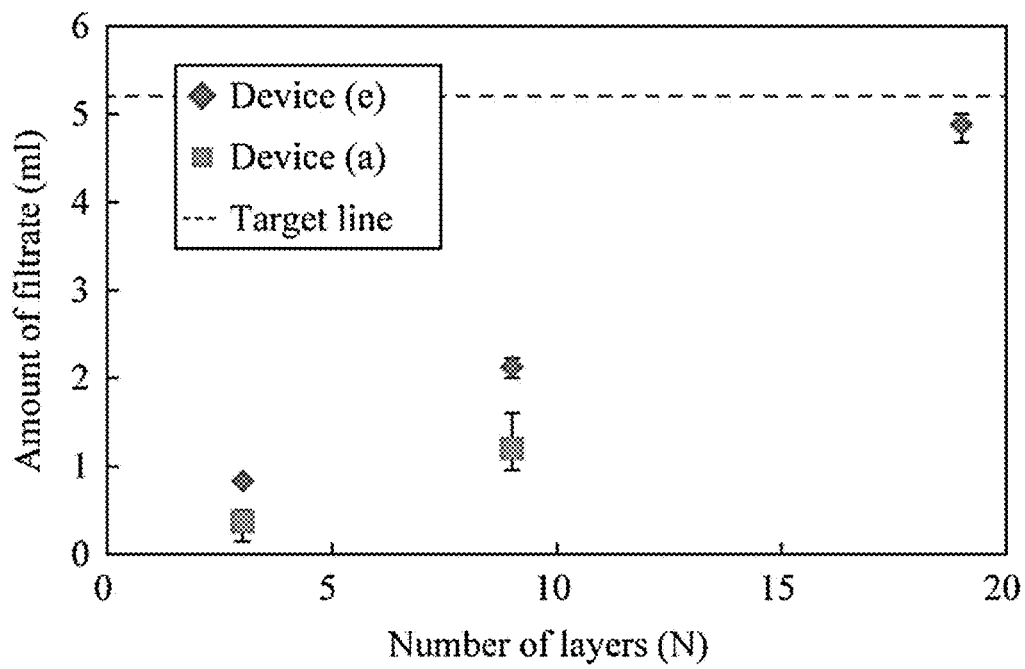
FIG. 20 is a graph showing the relationship between the number of stacked layers and the amount of filtrate.
Figure 21:
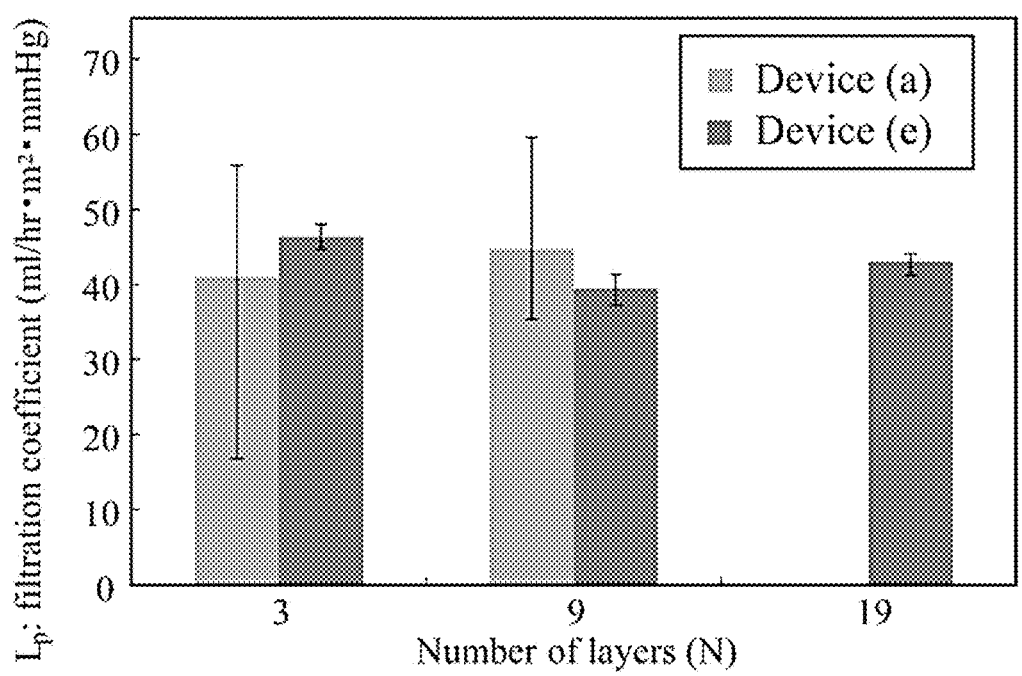
FIG. 21 is a graph showing the relationship between the number of stacked layers and the filtration coefficient.

<2.3> Results of Permeability Evaluation Experiment of a Device with a Stacked-Layer Structure FIG. 20 shows the amounts of filtrate obtained with the devices of FIGS. 18A and 18E. The number of stacked layers is in proportion to the amount of filtrate. When 19 dialysis membranes were used, the amount of filtrate nearly equivalent to the target value was obtained. Further, FIG. 21 shows the results of calculating filtration coefficients of the devices of FIGS. 18A and 18E using Formula (1) shown in 1.5 above and comparing the calculation results therebetween. With the device having an enlarged effective area of the membrane and an increased number of stacked layers, the same filtration coefficient as that of the device previously developed was able to be obtained.

<3> Conclusion (1) The relationship between biofouling and the flow path largely depends on the surface condition of the flow path, and mirror machining using electrolytic etching is suitable for the present device. (2) The device was formed in a hexagonal shape so as to have more number of portions to be screwed, and thus the leakage of blood was suppressed and stable dialysis performance was secured. (3) With a view to conducting a long-term in vivo experiment, the device having dialysis performance suitable for experiment for being implanted in a medium-sized dog was developed.

Although the embodiments of the present invention have been described in detail, the present invention is not limited thereto, and various design changes can be made within the spirit and scope of the present invention described in the scope of the claims. For example, the aforementioned embodiments have been described in detail for an easy understanding of the present invention, and the present invention is not necessarily limited to the embodiments that include all the configurations that have been described. Further, a configuration of an embodiment can be partially replaced with a configuration of another embodiment, and it is also possible to add a configuration of an embodiment to a configuration of another embodiment. Furthermore, part of a configuration of each of embodiments can include another configuration added thereto, be deleted, and be replaced with another configuration.

DESCRIPTION OF SYMBOLS

1 Hemofiltration device
2 Main body portion
3 Blood inlet
4 Blood outlet
5 Filtrate outlet
6 Bolt
21 Blood flow path layer
22 Plate member
23 Slot
24 Blood flow-in portion
25 Blood flow-out portion
26 Filtrate passing hole
31 Filtrate flow path layer
32 Plate member
33 Slot
34 Blood passing hole
35 Blood passing hole
36 Filtrate flow-out portion
41 Filtration membrane
51 First end plate
61 Second end plate

What is claimed is:

1. A hemofiltration device adapted to be implanted in a body of a mammal for filtering blood, comprising a main body which comprises:
a blood flow path layer having a blood flow path;
a filtrate flow path layer having a filtrate flow path disposed along the blood flow path; and
a filtration membrane interposed between the blood flow path layer and the filtrate flow path layer, the filtration membrane being adapted to filter blood flowing through the blood flow path,
wherein the filtration membrane is provided with blood passing holes and a filtrate passing hole, the blood passing holes are respectively disposed at a position continuous with a blood flow-in portion and a blood flow-out portion, and the filtrate passing hole is disposed at a position continuous with a filtrate flow-out portion,
wherein the blood flow path layer and the filtrate flow path layer are alternately stacked with the filtration membrane interposed therebetween,
wherein a filtrate outlet of the filtrate flow path is provided at a position closer to a blood outlet of the blood flow path than to a blood inlet of the blood flow path, and
wherein the blood inlet, the blood outlet, and the filtrate outlet are provided in a direction in which the blood flow path layer and the filtrate flow path layer are stacked.

2. The hemofiltration device according to claim 1, wherein the main body portion has a pentagonal or more polygonal outline or a circular outline, and is configured to be integrally formed in a state compressed in the stacked direction of the layers, by means of more than five fastening means equidistantly disposed along the outline.

3. The hemofiltration device according to claim 1, wherein:
the blood flow path has at least one fold-back portion, and
in the fold-back portion, a radius of curvature of a wall surface on an outer periphery side of the blood flow path is larger than that on an inner periphery side of the blood flow path.

4. The hemofiltration device according to claim 1, wherein:
the blood flow path layer has a slot and the filtrate flow path layer has a slot, the slots at least partially overlapping each other, and
each of the slot of the blood flow path layer and the slot of the filtrate flow path layer has any of zigzag, tree, and concentric circular shapes.

5. The hemofiltration device according to claim 1, wherein a surface roughness of the wall surface of the blood flow path has one of a maximum height Rz of 0.01 to 10 μm, inclusive or an arithmetic average roughness Ra of 0.01 to 3 μm, inclusive.

6. A hemofiltration device, comprising:
a blood flow path layer having a blood flow path provided with an input and an output;
a filtrate flow path layer having a filtrate flow path disposed along the blood flow path, the filtrate flow path provided with an output;
a filtration membrane, interposed between the blood flow path layer and the filtrate flow path layer, configured to filter blood of a mammal flowing from the input to the output of the blood flow path; and,
a main body portion in which the blood flow path layer and the filtrate flow path layer are alternately stacked with the filtration membrane interposed therebetween and first cross sections of the filtrate flow path layer and the filtration membrane form a blood inlet coupled to the input of the blood flow path, the main body including a filtrate outlet coupled to the output of the filtrate flow path and a blood outlet coupled to the output of the blood flow path.

7. The hemofiltration device according to claim 6, wherein second cross sections of the blood flow path layer and the filtration membrane form the filtrate outlet.

8. The hemofiltration device according to claim 6, wherein third cross sections of the filtrate flow path layer and the filtration membrane form the blood outlet.

9. The hemofiltration device according to claim 6, wherein each of the filtrate outlet, the blood inlet and the blood outlet is provided on one side of the main body portion.

10. The hemofiltration device according to claim 6, wherein the blood inlet and the blood outlet are provided on one side of the main body portion, and the filtrate outlet is provided on the opposite side from the one side of the main body.

11. The hemofiltration device according to claim 6, wherein the main body portion has a pentagonal or more polygonal outline or a circular outline, and is configured to be integrally formed in a state compressed in the stacked direction of the layers.

12. The hemofiltration device according to claim 6, wherein the blood flow path has at least one fold-back portion, and
a radius of curvature of a wall surface on an outer periphery side of the blood flow path is larger than that on an inner periphery side of the blood flow path in the fold-back portion.

13. The hemofiltration device according to claim 6, wherein:
the blood flow path layer has a first slot and the filtrate flow path layer has a second slot partially overlapped with the first slot, and
the first and second slot respectively have any of zigzag, tree, and concentric circular shapes.

14. The hemofiltration device according to claim 6, wherein a surface roughness of the wall surface of the blood flow path has one of a maximum height Rz of 0.01 to 10 μm, inclusive or an arithmetic average roughness Ra of 0.01 to 3 μm, inclusive.

15. A hemofiltration device, comprising:
a blood flow path layer having a blood flow path provided with an input;
a filtrate flow path layer having a filtrate flow path disposed along the blood flow path, the filtrate flow path provided with an output;
a filtration membrane configured to filter blood of a mammal flowing through the blood flow path;
a filtrate outlet coupled to the output of the filtrate flow path; and,
a blood inlet coupled to the input of the blood flow path, wherein the blood flow path layer and the filtrate flow path layer are alternately stacked with the filtration membrane interposed therebetween and first cross sections of the filtrate flow path layer and the filtration membrane form the blood inlet.

16. The hemofiltration device according to claim 15, wherein the blood inlet and the blood outlet are configured to be bypass-connected to a blood vessel.

17. The hemofiltration device according to claim 15, the filtrate outlet discharges filtrate therefrom.

18. The hemofiltration device according to claim 15, wherein second cross sections of the blood flow path layer and the filtration membrane form the filtrate outlet.

19. The hemofiltration device according to claim 15, wherein third cross sections of the filtrate flow path layer and the filtration membrane form the blood outlet.

20. The hemofiltration device according to claim 15, wherein the blood flow path is provided with an output,
the hemofiltration device further comprising a blood outlet coupled to the output of the blood flow path.

21. A method of filtering blood of a mammal, comprising:
preparing a hemofiltration device including:
a blood flow path layer having a blood flow path provided with an input and an output;
a filtrate flow path layer having a filtrate flow path disposed along the blood flow path, the filtrate flow path provided with an output;
a filtration membrane configured to filter blood of a mammal flowing from the input to the output of the blood flow path;
a filtrate outlet coupled to the output of the filtrate flow path;
a blood inlet coupled to the input of the blood flow path; and,
a blood outlet coupled to the output of the blood flow path,
wherein the blood flow path layer and the filtrate flow path layer are alternately stacked with the filtration membrane interposed therebetween and first cross sections of the filtrate flow path layer and the filtration membrane form the blood inlet,
bypass-connecting the blood inlet and the blood outlet to a blood vessel of the mammal; and,
discharging a filtrate from the filtrate outlet.

22. The method of filtering the blood of the mammal according to the claim 21, further comprising:
implanting the hemofiltration device in a body of the mammal.

23. The method of filtering the blood of the mammal according to the claim 21, further comprising:
connecting the filtrate outlet to a ureter of the mammal.

24. The method of filtering the blood of the mammal according to the claim 21, further comprising:
taking out the discharged filtrate outside a body of the mammal.

* * * * *